United States Patent [19]
Adamou et al.

[11] Patent Number: 5,811,535
[45] Date of Patent: Sep. 22, 1998

[54] HUMAN CARTILEGE GP39-LIKE GENE

[75] Inventors: Julie Adamou, Exton; Robert Kirkpatrick, King of Prussia; Martin Rosenberg, Royersford, all of Pa.

[73] Assignee: SmithKline Beecham Corporation, Philadelphia, Pa.

[21] Appl. No.: 694,915

[22] Filed: Aug. 9, 1996

[51] Int. Cl.$^6$ .................................................. C07H 21/04
[52] U.S. Cl. .................. 536/23.5; 536/23.1; 530/300; 530/350; 435/69.1; 435/172.3
[58] Field of Search ..................................... 530/300, 350; 536/23.1, 24.31, 24.3; 556/23.5; 435/172.3, 69.1

[56] References Cited

PUBLICATIONS

Lazar et al Molecular and Cellular Biology vol. 8 No. 3 1247–1252, Mar. 1988.
Burgess et al Journal of Cell Biology vol. 111 2129–2138, Nov. 1990.
Hakala et al Journal of Biological Chemistry vol. 268 no. 34 25803–25810, Dec. 1993.
Bartzer et al Nucleic Acid Research vol. 18 No. 23 6793–6798, 1990.
Watanabe, et al., "Identification of Glutamic Acid 204 and Aspartic Acid 200 in Chitinase A1 of *Bacillus circulans* WL–12 as Essential Residues for Chitinase Activity", (1993), Journal of Biological Chemistry, vol. 268, No. 25, pp. 18567–18572.
Shackelton, et al., "Identification of a 38–kDa Heparin–binding Glycoprotein (gp38k) in Differentiating Vascular Smooth Muscle Cells as a Member of a Group of Proteins Associated with Tissue Remodeling", (1995), Journal of Biological Chemistry, vol. 270, No. 22, pp. 13076–13083.
Renkema, et al., "Purification and Characterization of Human Chitotriosidase, a Novel Member of the Chitinase Family of Proteins", (1995), Journal of Biological Chemistry, vol. 270, pp. 2198–2202.
Nyirkos, et al., "Human synovial cells secrete a 39 kDa protein similar to a bovine mammary protein expressed during the non–lactating period", (1990), Biochem. J., vol. 268, pp. 265–268.
Rejman, et al., "Isolation and Characterization of a Novel 39 Kilodalton Whey Protein From Bovine Mammary Secretions Collected During the Nonlactating Period", (1988), Biochemical & Biophysical Research Communications, vol. 150, No. 1, pp. 329–334.
Boot, et al., "Cloning of a cDNA Encoding Chitotriosidase, a Human Chitinase Produced by Macrophages", (1995), Journal of Biological Chemistry, vol. 270, No. 44, pp. 26252–26256.
Hakala, et al., "Human Cartilage gp–39, a Major Secretory Product of Articular Chondrocytes and Synovial Cells, Is a Mammalian Member of a Chitinase Protein Family", (1993), Journal of Biological Chemistry, vol. 268, No. 34, pp. 25803–25810.
Johansen, et al., "Identification of Proteins Secreted by Human Osteoblastic Cells in Culture", (1992), Journal of Bone and Mineral Research, vol. 7, No. 5, pp. 501–511.
Morrison, et al., "neu and ras initiate murine mammary tumors that share genetic markers generally absent in e–mye and int–2–initiated tumors", (1994), Oncogene, vol. 9, pp. 3417–3426.
Johansen, et al., "Serum YKL–40: a New Potential Marker of Prognosis and Location of Metastases of Patients With Recurrent Breast Cancer", (1995), Eur. J. Cancer, vol. 31A, pp. 1437–1442.
Arias, et al., "Complementary Deoxyribonucleic Acid Cloning and Molecular Characterization of an Estrogen–Dependent Human Oviductal Glycoprotein", (1994), Biology of Reproduction, vol. 51, pp. 685–694.
Kirkpatrick, R.B., Matico, R.E., McNulty, D.E., Strickler, J.E., Rosenberg, M., "An abundantly secreted glycoprotein from *Drosophila melanogaster* is related to mammalian secretory proteins produced in rheumatoid tissues and by activated macrophages", (1995), Gene, vol. 153, pp. 147–154.
Hu, B., Kien, T., Figueira, W.F. and Price, P.A., "Isolation and Sequence of A Novel Human Chondrocyte Protein Related to Mammalian Members of the Chitinase Protein Family", (1996), Journal of Biological Chemistry, vol. 271, pp. 19415–19420.

*Primary Examiner*—Sheela Huff
*Assistant Examiner*—Julie R. Reeves
*Attorney, Agent, or Firm*—Ratner & Prestia; William T. Han; William T. King

[57] ABSTRACT

HC gp39-L polypeptides and DNA (RNA) encoding such HC gp39-L and a procedure for producing such polypeptides by recombinant techniques is disclosed. Also disclosed are methods for utilizing such HC gp39-L for the treatment of rheumatoid and osteoarthritis, osteoporosis, artherosclerosis, metastatic cancers, periodontia, chronic renal diseases, etc. Antagonists against such HC gp39-L and their use as a therapeutic to treat rheumatoid and osteoarthritis, osteoporosis, artherosclerosis, metastatic cancers, periodontia, chronic renal diseases, etc. are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the HC gp39-L and for detecting altered levels of the polypeptide in a host.

16 Claims, 6 Drawing Sheets

FIG. 1A

```
AGAGAATGTGTATCCCAGAAGAAGCTGGCCAAGGATATGGGAGCAACCACCATGGACCAG    60
                                                     M  D  Q    3
AAGTCTCTCTGGGCAGGTGTAGTGGTCTTGCTGCTTCTCCAGGGAGGATCTGCCTACAAA   120
 K  S  L  W  A  G  V  V  V  L  L  L  L  Q  G  G  S  A  Y  K    23
CTGGTTTGCTACTTTACCAACTGGTCCCAGGACCGGCAGGAACCAGGAAAATTCACCCCT   180
 L  V  C  Y  F  T  N  W  S  Q  D  R  Q  E  P  G  K  F  T  P    43
GAGAATATTGACCCCTTCCTATGCTCTCATCTCATCTATTCATTCGCCAGCATCGAAAAC   240
 E  N  I  D  P  F  L  C  S  H  L  I  Y  S  F  A  S  I  E  N    63
AACAAGGTTATCATCAAGGACAAGAGTGAAGTGATGCTCTACCAGACCATCAACAGTCTC   300
 N  K  V  I  I  K  D  K  S  E  V  M  L  Y  Q  T  I  N  S  L    83
AAAACCAAGAATCCCAAACTGAAAATTCTCTTGTCCATTGGAGGGTACCTGTTTGGTTCC   360
 K  T  K  N  P  K  L  K  I  L  L  S  I  G  G  Y  L  F  G  S    103
AAAGGGTTCCACCCTATGGTGGATTCTTCTACATCACGCTTGGAATTCATTAACTCCATA   420
 K  G  F  H  P  M  V  D  S  S  T  S  R  L  E  F  I  N  S  I    123
ATCCTGTTTCTGAGGAACCATAACTTTGATGGACTGGATGTAAGCTGGATCTACCCAGAT   480
 I  L  F  L  R  N  H  N  F  D  G  L  D  V  S  W  I  Y  P  D    143
CAGAAAGAAAACACTCATTTCACTGTGCTGATTCATGAGTTAGCAGAAGCCTTTCAGAAG   540
 Q  K  E  N  T  H  F  T  V  L  I  H  E  L  A  E  A  F  Q  K    163
GACTTCACAAAATCCACCAAGGAAAGGCTTCTCTTGACTGCGGGCGTATCTGCAGGGAGG   600
 D  F  T  K  S  T  K  E  R  L  L  L  T  A  G  V  S  A  G  R    183
CAAATGATTGATAACAGCTATCAAGTTGAGAAACTGGCAAAAGATCTGGATTTCATCAAC   660
 Q  M  I  D  N  S  Y  Q  V  E  K  L  A  K  D  L  D  F  I  N    203
CTCCTGTCCTTTGACTTCCATGGGTCTTGGGAAAAGCCCCTTATCACTGGCCACAACAGC   720
 L  L  S  F  D  F  H  G  S  W  E  K  P  L  I  T  G  H  N  S    223
CCTCTGAGCAAGGGGTGGCAGGACAGAGGGCCAAGCTCCTACTACAATGTGGAATATGCT   780
 P  L  S  K  G  W  Q  D  R  G  P  S  S  Y  Y  N  V  E  Y  A    243
GTGGGGTACTGGATACATAAGGGAATGCCATCAGAGAAGGTGGTCATGGGCATCCCCACA   840
 V  G  Y  W  I  H  K  G  M  P  S  E  K  V  V  M  G  I  P  T    263
TATGGGCACTCCTTCACACTGGCCTCTGCAGAAACCACCGTGGGGGCCCCTGCCTCTGGC   900
 Y  G  H  S  F  T  L  A  S  A  E  T  T  V  G  A  P  A  S  G    283
CCTGGAGCTGCTGGACCCATCACAGAGTCTTCAGGCTTCCTGGCCTATTATGAGATCTGC   960
 P  G  A  A  G  P  I  T  E  S  S  G  F  L  A  Y  Y  E  I  C    303
CAGTTCCTGAAAGGAGCCAAGATCACGCGGCTCCAGGATCAGCAGGTTCCCTACGCAGTC  1020
 Q  F  L  K  G  A  K  I  T  R  L  Q  D  Q  Q  V  P  Y  A  V    323
AAGGGGAACCAGTGGGTGGGCTATGATGATGTGAAGAGTATGGAGACCAAGGTTCAGTTC  1080
```

FIG. 1B

```
K   G   N   Q   W   V   G   Y   D   D   V   K   S   M   E   T   K   V   Q   F              343
TTAAAGAATTTAAACCTGGGAGGAGCCATGATCTGGTCTATTGACATGGATGACTTCACT                              1140
L   K   N   L   N   L   G   G   A   M   I   W   S   I   D   M   D   D   F   T              363
GGCAAATCCTGCAACCAGGGCCCTTACCCTCTTGTCCAAGCAGTCAAGAGAAGCCTTGGC                              1200
G   K   S   C   N   Q   G   P   Y   P   L   V   Q   A   V   K   R   S   L   G              383
TCCCTGTGAAGGATTAACTTACAGAGAAGCAGGCAAGATGACCTTGCTGCCTGGGGCCTG                              1260
S   L   *                                                                                  403
CTCTCTCCCAGGAATTCTCATGTGGGATTCCCCTTGCCAGGATGGCCTTTGGATCTCTCT                              1320
TCCAAGCCTTTCCTGACTTCCTCTTAGATCATAGATTGGACCTGGTTTTGTTTTCCTGCA                              1380
        GCTGTTGACTTGTTGCCCTGAAGTACAATAAAAAAAATTCATTTTGCTCCAGT                              1433
```

FIG. 2A

```
AGAGAATGTGTATCCCAGAAGAAGCTGGCCAAGGATATGGGAGCAACCACCATGGACCAG        60
                                                  M  D  Q          3
AAGTCTCTCTGGGCAGGTGTAGTGGTCTTGCTGCTTCTCCAGGGAGAGATGGGGTTTTGC       120
 K  S  L  W  A  G  V  V  V  L  L  L  L  Q  G  E  M  G  F  C        23
TATGTTGCCAGAGCTGGTCTTGAACTCCTGGGCTCAAGAAGTCCTCCTGCCTCAGCCTCC       180
 Y  V  A  R  A  G  L  E  L  L  G  S  R  S  P  P  A  S  A  S        43
CAAAGTGCTGGGATAACAGGATCTGCCTACAAACTGGTTTGCTACTTTACCAACTGGTCC       240
 Q  S  A  G  I  T  G  S  A  Y  K  L  V  C  Y  F  T  N  W  S        63
CAGGACCGGCAGGAACCAGGAAAATTCACCCCTGAGAATATTGACCCCTTCCTATGCTCT       300
 Q  D  R  Q  E  P  G  K  F  T  P  E  N  I  D  P  F  L  C  S        83
CATCTCATCTATTCATTCGCCAGCATCGAAAACAACAAGGTTATCATCAAGGACAAGAGT       360
 H  L  I  Y  S  F  A  S  I  E  N  N  K  V  I  I  K  D  K  S       103
GAAGTGATGCTCTACCAGACCATCAACAGTCTCAAAACCAAGAATCCCAAACTGAAAATT       420
 E  V  M  L  Y  Q  T  I  N  S  L  K  T  K  N  P  K  L  K  I       123
CTCTTGTCCATTGGAGGGTACCTGTTTGGTTCCAAAGGGTTCCACCCTATGGTGGATTCT       480
 L  L  S  I  G  G  Y  L  F  G  S  K  G  F  H  P  M  V  D  S       143
TCTACATCACGCTTGGAATTCATTAACTCCATAATCCTGTTTCTGAGGAACCATAACTTT       540
 S  T  S  R  L  E  F  I  N  S  I  I  L  F  L  R  N  H  N  F       163
GATGGACTGGATGTAAGCTGGATCTACCCAGATCAGAAAGAAAACACTCATTTCACTGTG       600
 D  G  L  D  V  S  W  I  Y  P  D  Q  K  E  N  T  H  F  T  V       183
CTGATTCATGAGTTAGCAGAAGCCTTTCAGAAGGACTTCACAAAATCCACCAAGGAAAGG       660
 L  I  H  E  L  A  E  A  F  Q  K  D  F  T  K  S  T  K  E  R       203
CTTCTCTTGACTGCGGGCGTATCTGCAGGGAGGCAAATGATTGATAACAGCTATCAAGTT       720
 L  L  L  T  A  G  V  S  A  G  R  Q  M  I  D  N  S  Y  Q  V       223
GAGAAACTGGCAAAAGATCTGGATTTCATCAACCTCCTGTCCTTTGACTTCCATGGGTCT       780
 E  K  L  A  K  D  L  D  F  I  N  L  L  S  F  D  F  H  G  S       243
TGGGAAAAGCCCCTTATCACTGGCCACAACAGCCCTCTGAGCAAGGGGTGGCAGGACAGA       840
 W  E  K  P  L  I  T  G  H  N  S  P  L  S  K  G  W  Q  D  R       263
GGGCCAAGCTCCTACTACAATGTGGAATATGCTGTGGGGTACTGGATACATAAGGGAATG       900
 G  P  S  S  Y  Y  N  V  E  Y  A  V  G  Y  W  I  H  K  G  M       283
CCATCAGAGAAGGTGGTCATGGGCATCCCCACATATGGGCACTCCTTCACACTGGCCTCT       960
 P  S  E  K  V  V  M  G  I  P  T  Y  G  H  S  F  T  L  A  S       303
GCAGAAACCACCGTGGGGGCCCCTGCCTCTGGCCCTGGAGCTGCTGGACCCATCACAGAG      1020
 A  E  T  T  V  G  A  P  A  S  G  P  A  A  G  P  I  T  E         323
TCTTCAGGCTTCCTGGCCTATTATGAGATCTGCCAGTTCCTGAAAGGAGCCAAGATCACG      1080
```

FIG. 2B

```
S   S   G   F   L   A   Y   Y   E   I   C   Q   F   L   K   G   A   K   I   T        343
CGGCTCCAGGATCAGCAGGTTCCCTACGCAGTCAAGGGGAACCAGTGGGTGGGCTATGAT              1140
R   L   Q   D   Q   Q   V   P   Y   A   V   K   G   N   Q   W   V   G   Y   D        363
GATGTGAAGAGTATGGAGACCAAGGTTCAGTTCTTAAAGAATTTAAACCTGGGAGGAGCC              1200
D   V   K   S   M   E   T   K   V   Q   F   L   K   N   L   N   L   G   G   A        383
ATGATCTGGTCTATTGACATGGATGACTTCACTGGCAAATCCTGCAACCAGGGCCCTTAC              1260
M   I   W   S   I   D   M   D   D   F   T   G   K   S   C   N   Q   G   P   Y        403
CCTCTTGTCCAAGCAGTCAAGAGAAGCCTTGGCTCCCTGTGAAGGATTAACTTACAGAGA              1320
P   L   V   Q   A   V   K   R   S   L   G   S   L   *                                423
AGCAGGCAAGATGACCTTGCTGCCTGGGGCCTGCTCTCTCCCAGGAATTCTCATGTGGGA              1380
TTCCCCTTGCCAGGATGGCCTTTGGATCTCTCTTCCAAGCCTTTCCTGACTTCCTCTTAG              1440
ATCATAGATTGGACCTGGTTTTGTTTTCCTGCAGCTGTTGACTTGTTGCCCTGAAGTACA              1500
ATAAAAAAAATTCATTTTGCTCCAGT                                                1526
```

FIG. 3A

```
GCCAAGGCAGGAGGGGCGCTTGAGCCCAGGAATTCAAGACCAGCCTGGGTAATGTAGTGA
GACCCTGTNTNNACAAATTTTTTTTTTTTTTTTAATTAGCAAGGTGTAAGGTGCATGCC
TGTGGNTCCAGCTACTCTGGAGGCCAAGCTGGGAAGATCCTTTGAGCCCGGGAGGTTGAG
GNTGCAGTGAGCCATGATGGTGCCATTGCACTCCAATTGGGGTGATACAGCAAGAGCAAG
ATCCTGTTTCTAAAAAAATTAAGCAAGCCAGAGGTGGCTGTGAACACAGAGAGAGGTCGG
GGGCATAGAAGAAGGAGACAGATTGGGATGATGAGGAAGGAGATTCAGGGCCGAGGGTGA
TACCAGGAGGCAGAGCCTGAGTATCACCTCCTTCCTTCTCCAGGACCGGGTCCCTTTTA
GGTGAGACTAGATGAAAAGGGCTCTTCAGCAGCTGACTTCACAGCAACTAATTTCTGACA
GGTCAGAGTTGGCATTGCTCAAATCTGGGCTTCATTTCCAAGAAGTTTCACAAGTACTGC
CAGGGGAAGTACCCTGGACTTCTTGCTTCTTTCGTGTAGGACAGGCTGTCGAAACCTCAG
TGGATAAAAGACCTAGAGAATGTGTATCCCAGAAGAAGCTGGCCAAGGATATGGGAGCAA
CCACCATGGACCAGAAGTCTCTCTGGGCAGGTGAGCATGGGGTTGATAATTCAGCAGGAA
      M   D   Q   K   S   L   W   A   G
AGTTGGTGAGGAAGGAAGAGGTAACAGGTCTGTAGAAGAAGTAATCTTCCTCCTTTCCTG
GGACTTCAGTCTTTCCGTTGACCTTAGTGTCAAAAAATTTCAAGCCAATGCAACTGTTGT
AGGGGAACCACCTGATCTTTCCTGAATGGACAAAAATGCAGCAGTAGCCAGAACCCTTTG
CACTGGCAGGATGTTCTCAGTTTGTGCAGAGGTCCTTCTTGTCCACATTAGAACTGGAGC
TAAGACAGGAAAGAGGCCAAGCTTTCTTAGTCTCTTGGTGTATGAGCGTTGTATTGCGAG
TCACATCTTTCTTGGGCTCTGCTGTGGTTATATTTTACAACTTTTGGAGAGCCCCACATT
TCTCATCTGCAGAATGGTTTATTGAATTTAATGTTTTTAAACTCTCCCTTTCAACTCTA
AAGTTCTGATCCAAAACTCTGGCTTTTGTGGTGGCTGGGAATTGGGATGAGAGTGGGGAT
GAGGCTAAATAAACAAGGCTATGAGTGAACGGGGACGTTTACCAGGAGGGGAGGGGAGG
GAATATGTCTGCTGGAGGAAAGAAATCATTTATTTGTGTCCATACCTCTTTCACCCTTGT
CTTACCCTCTCAAGCCATGAAGCCCCCACTTGGCAAGAGCCTTTTGGGTTCCTGTTGAAC
TTAGCTGAGCCCTGGACTGACCCTTGACAGGGTAGAGCCCGTAGGGAGGCCACACTTTGG
AGAAGGGCCTGGAGGCTGACCTGACAGTGGATGTGCCACAGAGAATTTCTCTGACCATTT
ACTTAGTGAGTGTGTGGAGAACCAGGGCCTAACCTCCCTGCCTAAAAAAACATGTGAGTC
ATCAAGAGAGAACAGTAGAGCCCTGTTTTCCAGCCCTAAGCTCTGCAGGGGAGGAATCAG
CTCCAGCAGCTGTGTCATTGAAAGTTTTCTCTCCTTTTTGGCTGCCCCTTTCTTCACTTT
TGGACCCGTAAAGGTTTCAGAGTGAACAATATCCCCAGGCTGGGGGATTGCAGTTCCAG
GAGTCTTGTCCATTGGGCAAAGTTTCTAGGATCCAGGGGTCTGCTCTTTTTTTCCTTTAG
GAGGATGTGTTAAGTATAGAATAATCTCACCAGTCTTCCTAGGGTAGATGTCCTATGGAG
AAGAGACTGGGCATAATTTCAAACATATAAGTTTAAAGCACTACCAGGGCCAGCTCACAC
TGCTTATCTTGTTCTAAGAGTTAATTGTTTATACATAGTGGGACCATCTCAATTTGCCTG
AGATAGTTCTGGTTCAAGCTATCGTCCTAGGGAAATTATTAATAATGTTCCTTTTTACTC
```

FIG. 3B

```
TTTGAAGGGTCTCATTGGACAATAAACTATATGGTCACCCTACCTATATTCAACTCCAGA
CTGGACTATGAGCTCCTTGAGTGCAGGGAAGGCATTAACTGCATTATAATTTCCCCAGTG
TCCTGAGCAATGCTTAGCACAGAGCATATGATTCAATAAAACTTTGTTGGATAAATGAAT
GAAAAAATAAATTCCCAGCTTGGAACATGTTTCTGCCTAGGAATGTAGAGACACAAGGCA
CCCCAGGGCTGGGGACCTCAAGGTCCTATAAAGAAACCACAGGCCGGGCGCGGTGGCTCA
CGCCTGTAATCCCAGCACTTTGGGAGGCCGAGGCGGGCGGATCACGAGGTCAGGAGATCG
AGACCATCCCGGCTAAAACGGTGAAACCCCGTCTCTACTAAAAATACAAAAAATTAGCCG
GGCGTAGTGGCGGGCGCCTGTAGTCCCAGCTACTTGGGAGGCTGAGGCAGGAGAATGGCG
TGAACCCGGGAGGCGGAGCTTGCAGTGAGCCGAGATCACACCACTGCACTCCAGCCTGGG
CGACAGAGCGAGACTCCGTCTCAAAAAAAAAAAAAAAAAAAAGAAACCACAGCAGCTGTGG
CTGGGGAGCCCAGATGAAGTGTGGCTCTATCTTGTATGTGAGCACACCCACATTTTCACT
GCCATTATCTGGACAGCAGAACCAGGTTTGGCTCAACAGATTTCTCTTTCCACCCATCT
ATTGCAGGAGTAGTGGTCTTGCTGCTTCTCCAGGGAGGTAAGTAGTCAATAAGTCACTAC
         V  V  V  L  L  L  Q  G
CGCCTGGATCTCCTGGCTTGGGTGCTTTCATTTTTGATGTACAGTTTCTTTTTCTGCTAC
ATGCTTTTTCTCTTGATTACTCTCTCCGGTTCTGCCACTGACATATTTATGACACTGAGT
TTTTATTCTATCTTTTTGTGTATCCCTTGTTCTAGTTCTTTTTGAGCCACTCTCTCTCTC
ACCCCTCCCCCATAGCTGGCCTCAATATGTGTGTGTGAATACAAACATACACAATGTTTG
TATTATCTGTTTCTCTACTGATCTGTGTCATCCATCCATACATACATACTGAATCTTAGT
GCTCCATGGGTGTTTCATATGTTGGTGGTATCTCTGTCTCTCAATGTATTTTTTTTTAA
TTTTTTTGAGACAGGGTCTCACTGTAAGGTCCAGGCTGTAGTGCAGTGGTGTGACCNTGG
CTCANTGCAGCCTTGACCTCCCAGGCTCAAACAATCCCCCAACTTCAGCCTCCTTAGTAG
CTGAGANTACAGGCATGAACCACTACACCTGGCTAATTNTTAAATTTTTTGTAGAGATGG
                                                    E  M  G
GGTTTTGCTATGTTGCCACAGCTGGTCTTGAACTCCTGGGCTCAAGAAGTCNTCNNGCNT
 F  C  Y  V  A  T  A  G  L  E  L  L  G  S  R  S  X  X  A  S
CAGCCTCCCAAAGTGCNGGGATAACAGGTNTGAGGCCACTGTGCCCAGCCTCAGCGTATT
 A  S  Q  S  A  G  I  T
TCTTAACTGGGGTCTGGGTACTCAAGAGCCAGCACTAAAGGCCCAGGCAGAATGACCCTC
AGAGGCTCTGGCAGAATGAGCAAATGATGCAATGGCTGTACTTGGGGAGAAAATTGTGAC
TTTCTGGACTCTAAGGCAACAGCCGTGAGATCTCACTGGCTCTCTTCATTCTACTCCAGG
                                                           G
ATCTGCCTACAAACTGGTTTGCTACTTTACCAACTGGTCCCAGGACCGGCAGGAACCAGG
  S  A  Y  K  L  V  C  Y  F  T  N  W  S  Q  D  R  Q  E  P  G
AAAATTCACCCCTGAGAATAT
  K  F  T  P  E  N
```

HUMAN CARTILEGE GP39-LIKE GENE

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human cartilege glycoprotein 39 like gene, hereinafter referred to as "HC gp39-L".

BACKGROUND OF THE INVENTION

The generation or destruction of tissue requires constant reorganization and restructuring of the extracellular matrix (ECM) components including interstitial collagens, basement membrane collagen, fibronectin, laminin, aggrecan, and various proteoglycans. Heinegard and Oldberg, *FASEB J*. 1989, 3, 2042–2051; Woessner *FASEB J*. 1991, 5, 214–2154. Normal types of remodeling processes include embryonic development, post-partum involution of the uterus, ovulation, wound healing, and bone and growth plate remodeling. Woessner et al. *Steroids* 1989, 54, 491–499; Weeks et al. *Biochim Biophys Acta* 1976, 445, 205–214; Lepage and Gache *EMBO J*. 1990, 9, 3003–3012; Wride and Sanders *Dev-Dyn*. 1993, 198(3) 225–39. Similar processes also occur in disease states such as joint destruction in rheumatoid and osteoarthritis, periodontia and tumor cell metastasis. Thompson and Oegema *J Bone Joint Surg*. 1979, 61, 407–16; Reynolds et al. *Adv-Dent-Res*. 1994, 8(2) 312–9. One example of these processes is the migration of macrophages to the site of inflammation as in the case of synovial tissue in rheumatoid arthritis. Cutolo et al. *Clin. and Exper. Rheum*. 1993, 11, 331–339. The ECM components are regulated, in both normal and disease states, by various exogenous and endogenous factors. For example, in tumor formation, the differentiation state of the cell can increase the rate of degradation of the ECM. Benya *Pathol. Immunopatliol. Res*. 1988, 7, 51–54. Likewise, the presence of metalloproteinases or their inhibitors can alter the composition of the ECM. An imbalance of metalloproteinases and tissue inhibitors of matrix metalloproteinases (TIMP) has been shown to contribute to the pathogenesis of osteoarthritis. Dean et al. *J. Clin. Invest*. 1989, 84: 678–685. Cytokines, growth factors, and the extracellular environment can all contribute to the alteration of the ECM. Tyler *Biochem J*. 1985, 227, 869–878; Dinarello *Sem Immunol*. 1992, 4, 133–145; McConnell et al. *J Cell Biol*. 1987, 105, 1087–98.

The growth of cartilage and bone is actualized by cells such as articular chondrocytes and osteoblasts. The main function of these cells in immature tissue is the deposition and remodeling of the cartilage or bone matrix. In adult tissue, these cells maintain this matrix in order to ensure its proper function. In both cases, this encompasses secretion of the extracellular components as well as secretion of proteins involved in the turnover of the ECM.

A major species of protein secreted by these cells and involved in the turnover of the ECM are the metalloproteinases. Woessner *FASEB J*. 1991, 5, 214–2154. A new type of secretory glycoprotein has also been identified in human cartilage, osteoblasts, synovial cells, sheep and bovine oviduct and mammary cells, and macrophages. Nyrikos and Golds *Biochem J*. 1990, 268, 265–268; Hakala et al. *J. Biol. Chem*. 1993, 268(34) 25803–25810; Johansen et al. *J. Bone and Min. Res*. 1992, 7(5) 501–511; Rejman and Hurley *Biochem. Biophys. Res. Commun*. 1988, 150, 329–334; DeSouza and Murray *Endocrinology* 1995, 136(6) 2485–2496; Hollak et al. *J. Clin. Invest*. 1994, 93, 1288–92; Arias et al. *Biol. of Reproduction* 1994, 51, 685–694. These novel mammalian proteins all share regions of significant homology to the bacterial and fungal chitinases and, therefore, are referred to herein as "chitinase-like" proteins. Chitinases are enzymes that hydrolyze glycosidic bonds. They bear a subtle similarity to lysozymes from mammals and function as endoglycosidases with a specificity for N-acetyl-glucosamine linkages. However, these types of chitin-like structures, homopolymers of N-acetyl-glucosarine, are not normally encountered in mammalian tissue.

The human cartilage glycoprotein, HC gp-39, is a protein with an apparent molecular weight of approximately 39 kDa secreted by both articular chondrocytes and synovial fibroblasts. Nyrikos and Golds *Biochem J*. 1990, 268, 265–268; Hakala et al. *J. Biol. Chem*. 1993, 268(34), 25803–25810. This protein has been described as a marker for joint injury, appearing in the blood and synovial fluid from patients diagnosed with rheumatoid arthritis. Johansen et al. *British J. of Rheumatology* 1993, 32, 949–955. The gene encoding this protein has been cloned and is expressed specifically in cartilage and synovial cells of rheumatic joints. Hakala et al. *J. Biol. Chem*. 1993, 268(34), 25803–25810. The protein YKL-40 has also been identified as one of the major secretory products of cultured human osteoblastic cells (osteocarcinoma cell line MG-63) expressed in response to 1,25-dihydroxyvitamin D3 stimulation. Johansen et al. *J. Bone and Min. Res*. 1992, 7(5), 501–511; Johansen et al. *Br. J. Rheumatol*. 1993, 32, 949–55. The N-terminal portion of YKL-40 was sequenced and found to be identical to HC gp-39. Upon further sequencing, YKL-40 and HC gp-39 were found to be identical.

Chitotriosidase is an enzyme which has been identified as a member of this "chitinase-like" family. Renkema et al. *J. Biol Chem*. 1995, 27C, 2198–2202; Hollak et al. *J. Clin. Invest*. 1994, 93, 1288–92. This protein also has an apparent molecular weight of 39 kDa and shares N-terminal homologies with HC gp-39, the bovine mammary protein, and several bacterial chitinases. Activity of this enzyme was originally detected from cells of patients afflicted with Gaucher Disease (GD). Gaucher Disease is an inherited deficiency in the activity of glucocerebrosidase, a lysosomal hydrolase. This defect results in an accumulation of glucosylceramide (glucocerebroside) in the lysosomes of macrophages. Accumulation of lipid-laden macrophages results in hepatosplenomegaly, bone lesions, and neurological anomalies. After morphological differentiation of monocytes into macrophages in culture, the cells begin to produce and secrete increasing amounts of chitotriosidase. This increase is, on average, 600 times greater in GD patients than in patients with other pathological conditions. The elevation in chitotriosidase activity can be effectively reduced, however, upon initiation of enzyme supplementation therapy. Unlike the other members of the chitinase-like family, chitotriosidase has chitolytic activity. Like the bacterial enzyme, it has the ability to degrade chitin azure, a polymer of beta-1-4-linked N-acetylglucosamine moieties.

A new lymphocyte-associated protein of the chitinase-like family, referred to as HC gp-39L, has now been identified. HC-gp39L protein is believed to be involved in tissue remodeling in the mammalian cell and thus serve as useful tools in the development of therapeutics and diagnostics for tissue remodeling disorders, such rheumatoid and osteoarthritis, osteoporosis, artherosclerosis, metastatic cancers, periodontia, chronic renal diseases, etc. Further, we have discovered two forms of HC-gp39L as listed in SEQ ID NOS: [2] and [3] which are believed to be splice variants. Thus, as used herein, HC-gp39L refers to either splice variants.

SUMMARY OF THE INVENTION

Toward these ends, and others, it is an object of the present invention to provide polypeptides, inter alia, that have been identified as novel HC gp39-L by homology between the amino acid sequence set out in FIGS. 1A–B or 2A–B (SEQ ID NOS:[2] or [4]) and known amino acid sequence of HC gp-39.

It is a further object of the invention, moreover, to provide polynucleotides that encode HC gp39-L, particularly polynucleotides that encode the polypeptides herein designated as HC gp39-L.

In a particularly preferred embodiment of this aspect of the invention the polynucleotides comprise the region encoding HC gp39-L in the sequences set out in FIGS. 1A–B and 2A–B.

In accordance with this aspect of the invention there are provided isolated nucleic acid molecules encoding HC gp39-L, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives.

Among the particularly preferred embodiments of this aspect of the invention are naturally occurring allelic variants of HC gp39-L.

It also is an object of the invention to provide HC gp39-L polypeptides, particularly HC gp39-L polypeptides, that may be employed for therapeutic purposes, for example, to treat including, but not limited to, rheumatoid and osteoarthritis, osteoporosis, artherosclerosis, metastatic cancers, periodontia, chronic renal diseases, etc.

In accordance with this aspect of the invention there are provided novel polypeptides of human origin referred to herein as HC gp39-L as well as biologically, diagnostically or therapeutically useful fragments, variants and derivatives thereof, variants and derivatives of the fragments, and analogs of the foregoing.

Among the particularly preferred embodiments of this aspect of the invention are variants of HC gp39-L encoded by naturally occurring alleles of the HC gp39-L gene.

In accordance with another aspect of the present invention there are provided methods of screening for compounds which bind to and activate or inhibit activation of the polypeptides of the present invention.

It is another object of the invention to provide a process for producing the aforementioned polypeptides, polypeptide fragments, variants and derivatives, fragments of the variants and derivatives, and analogs of the foregoing.

In a preferred embodiment of this aspect of the invention there are provided methods for producing the aforementioned HC gp39-L polypeptides comprising culturing host cells having expressibly incorporated therein an exogenously-derived HC gp39-L-encoding polynucleotide under conditions for expression of HC gp39-L in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing HC gp39-L expression in cells by determining HC gp39-L polypeptides or HC gp39-L-encoding mRNA; to treat, but not limited to, rheumatoid and osteoarthritis, osteoporosis, artherosclerosis, metastatic cancers, periodontia, chronic renal diseases etc. in vitro, ex vivo or in vivo by exposing cells to HC gp39-L polypeptides or polynucleotides as disclosed herein; assaying genetic variation and aberrations, such as defects, in HC gp39-L genes; and administering a HC gp39-L polypeptide or polynucleotide to an organism to augment HC gp39-L function or remediate HC gp39-L dysfunction.

In accordance with still another embodiment of the present invention there is provided a process of using such activating compounds to stimulate the polypeptide of the present invention for the treatment of conditions related to the under-expression of the HC gp39-L.

In accordance with another aspect of the present invention there is provided a process of using such inhibiting compounds for treating conditions associated with over-expression of the HC gp39-L.

In accordance with yet another aspect of the present invention there is provided non-naturally occurring synthetic, isolated and/or recombinant HC gp39-L polypeptides which are fragments, consensus fragments and/or sequences having conservative amino acid substitutions, of at least one domain of the HC gp39-L of the present invention, such that the binding molecule may bind HC gp39-L, or which may also modulate, quantitatively or qualitatively HC gp39-L binding.

In accordance with still another aspect of the present invention there are provided synthetic or recombinant HC gp39-L polypeptides, conservative substitution and derivatives thereof, antibodies thereto, anti-idiotype antibodies, compositions and methods that can be useful as potential modulators of HC gp39-L function, which may be used in diagnostic, therapeutic and/or research applications.

It is still another object of the present invention to provide synthetic, isolated or recombinant polypeptides which are designed to inhibit or mimic various HC gp39-L or fragments thereof.

In accordance with certain preferred embodiments of this and other aspects of the invention there are provided probes that hybridize to HC gp39-L sequences.

In certain additional preferred embodiments of this aspect of the invention there are provided antibodies against HC gp39-L polypeptides. In certain particularly preferred embodiments in this regard, the antibodies are highly selective for HC gp39-L.

In accordance with another aspect of the present invention, there are provided HC gp39-L agonists. Among preferred agonists are molecules that mimic HC gp39-L, that bind to HC gp39-L-binding molecules, and that elicit or augment HC gp39-L-induced responses. Also among preferred agonists are molecules that interact with HC gp39-L gene or HC gp39-L polypeptides, or with other modulators of HC gp39-L activities, and thereby potentiate or augment an effect of HC gp39-L or more than one effect of HC gp39-L.

In accordance with yet another aspect of the present invention, there are provided HC gp39-L antagonists (inhibitors). Among preferred antagonists are those which mimic HC gp39-L so as to bind to HC gp39-L binding molecules but not elicit a HC gp39-L-induced response or more than one HC gp39-L-induced response. Also among preferred antagonists are molecules that bind to or interact with HC gp39-L so as to inhibit an effect of HC gp39-L or more than one effect of HC gp39-L or which prevent expression of HC gp39-L.

In a further aspect of the invention there are provided compositions comprising a HC gp39-L polynucleotide or a HC gp39-L polypeptide for administration to cells in vitro, to cells ex vivo and to cells in vivo, or to a multicellular organism. In certain particularly preferred embodiments of this aspect of the invention, the compositions comprise a HC gp39-L polynucleotide for expression of a HC gp39-L polypeptide in a host organism for treatment of disease. Particularly preferred in this regard is expression in a human patient for treatment of a dysfunction associated with aberrant endogenous activity of HC gp39-L.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1A and FIG. 1B show the nucleotide and deduced amino acid sequence of one splice variant of HC gp39-L.

FIG. 2A and FIG. 2B show the nucleotide and deduced amino acid sequence of the second splice variant of HC gp39-L.

FIG. 3A and FIG. 3B shows partial genomic nucleotide and deduced amino sequence of HC gp 39-L covering the region of splice variation.

GLOSSARY

The following illustrative explanations are provided to facilitate understanding of certain terms used frequently herein, particularly in the examples. The explanations are provided as a convenience and are not limitative of the invention.

"Digestion" of DNA refers to catalytic cleavage of a DNA with an enzyme such as but not limited to restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 μg of plasmid or DNA fragment is digested with about 2 units of enzyme in about 20 μl of reaction buffer. For the purpose of isolating DNA fragments for plasmid construction, typically 5 to 50 μg of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

"Genetic element" generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

"Isolated" means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below.

"Oligonucleotide(s)" refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example they code for toxins that greatly increase the virulence of pathogenic bacteria. They can also encode genes that confer resistance to antibotics. Plasmids are widely used in molecular biology as vectors used to clone and express recombinant genes. Plasmids generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Polynucleotide(s)" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia simple and complex cells.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182:626–646 (1990) and Rattan et al., Protein Synthesis: Posttranslational Modifications and Aging, Ann. N.Y. Acad. Sci. 663:48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same post-translational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

(1) A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

(2) A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

"Fusion proteins": EP-A-O 464 533 (Canadian counterpart 2045869) discloses fusion proteins comprising various portions of constant region of immunoglobin molecules together with another human protein or part thereof. In many cases, the Fc part in fusion protein is thoroghly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, shIL5-α has been fused with Fc portions for the purpose of high-throughput screening assays to identify antagonists of hIL-5. See, D. Bennett et al., Journal of Molecular Recognition, 8:52–58 (1995) and K. Johanson et al., The Journal of Biological Chemistry, 270:16, pp 9459–9471 (1995).

Thus, this invention also relates to genetically engineered soluble fusion proteins comprised from HC gp39-L, or a portion thereof, and of various portions of the constant regions of heavy or light chains of immunoglobulins of various subclass (IgG, IgM, IgA, IgE). Preferred as immunoglobulin is the constant part of the heavy chain of human IgG, particularly IgG1, where fusion takes place at the hinge region. In a particular embodiment, the Fc part can be removed in a simple way by a cleavage sequence which is also incorporated and can be cleaved with factor Xa. Furthermore, this invention relates to processes for the preparation of these fusion by genetic engineering, and to the use thereof for diagnosis and therapy. An yet further aspect of the invention also relates to polynucleotide encoding such fusion proteins.

Other examples of fusion protein technology can be found in WO94/29458 and WO94/22914.

"Binding molecules" (or otherwise called "interaction molecules") refer to molecules such as receptors or substrates that specifcally bind to or interact with polypeptides of the present invention. Included in the definition of binding molecules are other factors, co-factors, units or subunits within the apoptosis polypeptide of the present invention which enhance its activity or diminish it. Such binding molecules are a part of the present invention. Binding molecules also may be non-naturally occurring, such as antibodies and antibody-derived reagents that bind specifically to polypeptides of the invention.

"N" in the polynucleotide sequence means any on the nucleotide adenine (A), cytosine (C), guanine (G) or thymine (T).

DESCRIPTION OF THE INVENTION

The present invention relates to novel HC gp39-L polypeptides and polynucleotides, among other things, as described in greater detail below. In particular, the invention relates to polypeptides and polynucleotides of a novel HC gp39-L, which is related by amino acid sequence homology to HC gp39 polypeptide. The invention relates especially to HC gp39-L having the nucleotide and amino acid sequences set out in FIGS. 1 and 2, which are splice variants of each other. It will be appreciated that the nucleotide and amino acid sequences set out in FIGS. 1 and 2 are obtained by sequencing the cDNA of the deposited clones. Hence, the sequences of the deposited clones are controlling as to any discrepancies between the sequences disclosed in FIGS. 1 and 2, and any reference to the sequences of FIGS. 1 and 2 include reference to the sequence of the human cDNA of the deposited clones.

Polynucleotides

In accordance with one aspect of the present invention, there are provided isolated polynucleotides which encode the HC gp39-L polypeptide having the deduced amino acid sequence of FIGS. 1 or 2. Using the information provided herein, such as the polynucleotide sequence set out in FIGS. 1 or 2, a polynucleotide of the present invention encoding HC gp39-L polypeptide, may be obtained using standard cloning and screening procedures, such as those for cloning cDNAs using mRNA from cells from human thymus as starting material. Illustrative of the invention, the polynucleotide set out in FIGS. 1 or 2 is discovered in a cDNA library derived from cells of human thymus using the expressed sequence tag (EST) analysis (Adams, M. D., et al. (1991), Science 252:1651–1656; Adams, M. D., et al. (1992), Nature 355:632–634; Adams, M. D., et al. (1995), Nature 377 Supp, 3–174).

The cDNA sequences of HC gp 39-L obtained are set out in FIGS. 1 and 2. SEQ ID NOS: [1] and [3]. They contain open reading frames encoding proteins of 385 and 416 amino acid residues with deduced molecular weights of about 39 and 40 kDa. The protein exhibits greatest homology to HC GP39 protein among known proteins. HC gp39-L of FIGS. 1 and 2 have about 55% and 51% identity to HC GP39 DNA and protein sequence, respectively.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The coding sequence which encodes the polypeptide may be identical to the coding sequence of the polynucleotide shown in FIGS. 1 or 2. (SEQ ID NO: [1] or [3]) It also may be a polynucleotide with a different sequence, which, as a result of the redundancy (degeneracy) of the genetic code, also encodes the polypeptide of FIGS. 1 or 2. (SEQ ID NO: [2] or [4])

Polynucleotides of the present invention which encode the polypeptide of FIGS. 1 or 2 may include, but are not limited to the coding sequence for the mature polypeptide, by itself; the coding sequence for the mature polypeptide and additional coding sequences, such as those encoding a leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA; additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.), among others, many of which are commercially available. As described in Gentz et al., Proc. Natl. Acad. Sci., USA 86:821–824 (1989), for instance, hexa-histidine provides for convenient purification of the fusion protein. The HA tag corresponds to an epitope derived of influenza hemagglutinin protein, which has been described by Wilson et al., Cell 37:767 (1984), for instance.

Thus, it is the object of this invention to provide genomic polynucleotide sequence of HC gp39-L as shown in FIG. 3. SEQ ID NO: [5].

In accordance with the foregoing, the term "polynucleotide encoding a polypeptide" as used herein encompasses polynucleotides which include a sequence encoding a polypeptide of the present invention, particularly the HC gp39-L having the amino acid sequence set out in FIGS. 1 or 2. The term also encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIGS. 1 or 2. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of HC gp39-L set out in FIGS. 1 or 2; variants, analogs, derivatives and fragments thereof, and fragments of the variants, analogs and derivatives.

Further particularly preferred in this regard are polynucleotides encoding HC gp39-L variants, analogs, derivatives and fragments, and variants, analogs and derivatives of the fragments, which have the amino acid sequence of the HC gp39-L polypeptide of FIGS. 1 or 2 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the HC gp39-L. Also especially preferred in this regard are conservative substitutions. Most highly preferred are polynucleotides encoding polypeptides having the amino acid sequence of FIGS. 1 or 2, without substitutions.

Further preferred embodiments of the invention are polynucleotides that are at least 70% identical to a polynucleotide encoding the HC gp39-L polypeptide having the amino acid sequence set out in FIGS. 1 or 2, and polynucleotides which are complementary to such polynucleotides. Alternatively, most highly preferred are polynucleotides that comprise a region that is at least 80% identical to a polynucleotide encoding the HC gp39-L polypeptide of the human cDNA of the deposited clones and polynucleotides complementary thereto. In this regard, polynucleotides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Particularly preferred embodiments in this respect, moreover, are polynucleotides which encode polypeptides which retain substantially the same biological function or activity as the mature polypeptide encoded by the cDNA of FIGS. 1 or 2.

As discussed additionally herein regarding polynucleotide assays of the invention, for instance, polynucleotides of the invention as discussed above, may be used as a hybridization probe for cDNA and genobic DNA, to isolate full-length cDNAs and genomic clones encoding HC gp39-L and to isolate cDNA and genomic clones of other genes that have a high sequence similarity to the HC gp39-L gene. Such probes generally will comprise at least 15 nucleotides. Preferably, such probes will have at least 30 nucleotides and may have at least 50 nucleotides. Particularly preferred probes will have at least 30 nucleotides and will have 50 nucleotides or less.

For example, the coding region of the HC gp39-L gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to a HC gp39-L polypeptide which has the deduced amino acid sequence of FIGS. 1 or 2. SEQ ID NO: [2] or [4].

The invention also relates to fragments, analogs and derivatives of these polypeptides. The terms "fragment," "derivative" and "analog" when referring to the polypeptide of FIGS. 1 or 2, means a polypeptide which retains essentially the same biological function or activity as such polypeptide, i.e. functions as a HC gp39-L, or retains the ability to bind the binding molecules even though the polypeptide does not function as a HC gp39-L. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIGS. 1 or 2 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of HC gp39-L set out in FIGS. 1 or 2, variants, analogs, derivatives and fragments thereof, and variants, analogs and derivatives of the fragments. Further particularly preferred embodiments of the invention in this regard are polypeptides having the amino acid sequence of the HC gp39-L, variants, analogs, derivatives and fragments thereof, and variants, analogs and derivatives of the fragments which retains the activity/function of HC gp39-L.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Further particularly preferred in this regard are variants, analogs, derivatives and fragments, and variants, analogs and derivatives of the fragments, having the amino acid sequence of the HC gp39-L polypeptide of FIGS. 1 or 2, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the HC gp39-L. Also especially preferred in this regard are conservative substitutions. Most highly preferred are polypeptides having the amino acid sequence of FIGS. 1 or 2 without substitutions.

The polypeptides and polynucleotides of the present invention are preferably provided in an isolated form, and preferably are purified to homogeneity.

The polypeptides of the present invention include the polypeptide of SEQ ID NO:[2] or [4] (in particular the mature polypeptide) as well as polypeptides which have at least 80% identity to the polypeptide of SEQ ID NO:[2] or [4] and more preferably at least 90% similarity (more preferably at least 90% identity) to the polypeptide of SEQ ID NO:[2] or [4] and still more preferably at least 95% similarity (still more preferably at least 95% identity) to the polypeptide of SEQ ID NO:[2] or [4] and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotides sequences as determined by the identity of the match between two strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exist a number of methods to measure identity and similarity between two polynucleotide or polypeptide sequences, the terms "identity" and "similarity" are well known to skilled artisans (Carillo, H., and Lipman, D., SIAM *J. Applied Math.* 48:1073 (1988)). Methods commonly employed to determine identity or similarity between two sequences include, but are not limited to disclosed in Guide to Huge Computers, Martin J. Bishop, ed., Academic Press, San Diego, 1994, and Carillo, H., and Lipman, D., SIAM *J. Applied Math.* 48:1073 (1988). Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., *Nucleic Acids Research* 12(1):387 (1984)), BLASTP, BLASTN, FASTA (Atschul, S. F. et al., *J. Molec. Biol.* 215:403 (1990)).

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

Fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a HC gp39-L polypeptide of the present comprised within a precursor polypeptide designed for expression in a host and having heterologous pre and pro-polypeptide regions fused to the amino terminus of the HC gp39-L fragment and an additional region fused to the carboxyl terminus of the fragment. Therefore, fragments in one aspect of the meaning intended herein, refers to the portion or portions of a fusion polypeptide or fusion protein derived from HC gp39-L.

As representative examples of polypeptide fragments of the invention, there may be mentioned those which have from about 5–15, 10–20, 15–40, 30–55, 41–75, 41–80, 41–90, 50–100, 75–100, 90–115, 100–125, and 110–113 amino acids long.

In this context about includes the particularly recited range and ranges larger or smaller by several, a few, 5, 4, 3, 2 or 1 amino acid at either extreme or at both extremes. For instance, about 40–90 amino acids in this context means a polypeptide fragment of 40 plus or minus several, a few, 5, 4, 3, 2 or 1 amino acids to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids.

Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 amino acids long.

Among especially preferred fragments of the invention are truncation mutants of HC gp39-L. Truncation mutants include HC gp39-L polypeptides having the amino acid sequence of FIGS. 1 or 2, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of HC gp39-L. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of HC gp39-L.

Among highly preferred fragments in this regard are those that comprise regions of HC gp39-L that combine several structural features, such as several of the features set out above. In this regard, the regions defined by the residues about 10 to about 20, about 40 to about 50, about 70 to about 90 and about 100 to about 113 of FIGS. 1 or 2, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of HC gp39-L. Most highly preferred in this regard are fragments that have a chemical, biological or other activity of HC gp39-L, including those with a similar activity or an improved activity, or with a decreased undesirable activity. Highly preferred in this regard are fragments that contain regions that are homologs in sequence, or in position, or in both sequence and to active regions of related polypeptides, such as the related polypeptide of HC gp39. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, host cells, expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques. In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trp1 gene of S. cerevisiae.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include Escherichia coli, Bacillus subtilis and Salmonella typhimurium. Various species of Pseudomonas, Streptomyces, and Staphylococcus are suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., Cell 23:175 (1981). Other cell lines capable of expressing a compatible vector include for example, the C127, 3T3, CHO, HeLa, human kidney 293 and BHK cell lines.

Mammalian expression vectors will comprise an origin of replication, a suitable promoter and enhancer, and also any necessary ribosome binding sites, polyadenylation sites, splice donor and acceptor sites, transcriptional termination sequences, and 5' flanking non-transcribed sequences that are necessary for expression. In certain preferred embodiments in this regard DNA sequences derived from the SV40 splice sites, and the SV40 polyadenylation sites are used for required non-transcribed genetic elements of these types.

The HC gp39-L polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

HC gp39-L polynucleotides and polypeptides may be used in accordance with the present invention for a variety of applications, particularly those that make use of the chemical and biological properties of HC gp39-L. Additional applications relate to diagnosis and to treatment of disorders of cells, tissues and organisms. These aspects of the invention are illustrated further by the following discussion.

Polynucleotide assays

This invention is also related to the use of the HC gp39-L polynucleotides to detect complementary polynucleotides such as, for example, as a diagnostic reagent. Detection of a mutated form of HC gp39-L associated with a dysfunction will provide a diagnostic tool that can add or define a diagnosis of a disease or susceptibility to a disease which results from under-expression or over-expression or altered expression of HC gp39-L. Individuals carrying mutations in the HC gp39-L gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. PCR (Saiki et al., Nature 324:163–166 (1986)). RNA or cDNA may also be used in the same ways. As an example, PCR primers complementary to the nucleic acid encoding HC gp39-L can be used to identify and analyze HC gp39-L expression and mutations. For example, deletions and insertions can be detected by a change in size of the amplified product in comparison to the normal genotype. Point mutations can be identified by hybridizing amplified DNA to radiolabeled HC gp39-L RNA or alternatively, radiolabeled HC gp39-L anti-sense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science 230:1242 (1985)).

Sequence changes at specific locations also may be revealed by nuclease protection assays, such as RNase and S1 protection or the chemical cleavage method (e.g., Cotton et al., Proc. Natl. Acad. Sci., USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In accordance with a further aspect of the invention, there is provided a process for diagnosing rheumatoid and osteoarthritis, osteoporosis, artherosclerosis, metastatic cancers, periodontia, chronic renal diseases etc. or a susceptibility to such diseases/disorders. Thus, a mutation in HC gp39-L indicates a susceptibility to rheumatoid and osteoarthritis, osteoporosis, artherosclerosis, metastatic cancers, periodontia, chronic renal diseases etc. and the nucleic acid sequences described above may be employed in an assay for ascertaining such susceptibility. Thus, for example, the assay may be employed to determine a mutation in a HC gp39-L protein as herein described, such as a deletion, truncation, insertion, frame shift, etc., with such mutation being indicative of a susceptibility to the above disorders/diseases.

The invention provides a process for diagnosing, particularly rheumatoid and osteoarthritis, osteoporosis, artherosclerosis, metastatic cancers, periodontia, chronic renal diseases etc. comprising determining from a sample derived from a patient an abnormally decreased or increased level of expression of polynucleotide having the sequence of FIGS. 1 or 2 (SEQ ID NO: [1] or [3]). Decreased or increased expression of polynucleotide can be measured using any on of the methods well known in the art for the quantation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Chromosome assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with gene associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, because primers that span more than one exon could complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: A Manual of Basic Techniques, Pergamon Press, New York (1988).

As an example of how this is performed, HC GP39-L DNA is digested and purified with QIAEX II DNA purification kit (QIAGEN, Inc., Chatsworth, Calif.) and ligated to Super Cos1 cosmid vector (STRATAGENE, La Jolla, Calif.). DNA is purified using Qiagen Plasmid Purification Kit (QIAGEN Inc., Chatsworth, Calif.) and 1 mg is labeled by nick translation in the presence of Biotin-dATP using BioNick Labeling Kit (GibcoBRL, Life Technologies Inc., Gaithersburg, Md.). Biotinilation is detected with GENE-TECT Detection System (CLONTECH Laboratories, Inc. Palo Alto, Calif.). In situ Hybridization is performed on slides using ONCOR Light Hybridization Kit (ONCOR, Gaithersberg, Md.) to detect single copy sequences on metaphase chromosomes. Peripheral blood of normal donors is cultured for three days in RPMI 1640 supplemented with 20% FCS, 3% PHA and penicillin/streptomycin, synchronized with $10^{-7}$M methotrexate for 17 hours and is washed twice with unsupplemented RPMI. Cells are incubated with $10^{-3}$M thymidine for 7 hours. The cells are arrested in metaphase after 20 minutes incubation with colcemid (0.5 µg/ml) followed by hypotonic lysis in 75 mM KCl for 15 minutes at 37° C. Cell pellets are then spun out and fixed in Carnoy's fixative (3:1 methanol/acetic acid).

Metaphase spreads are prepared by adding a drop of the suspension onto slides and aid dried. Hybridization is performed by adding 100 ng of probe suspended in 10 ml of hybridization mix (50% formamide, 2×SSC, 1% dextran sulfate) with blocking human placental DNA 1 µg/ml), Probe mixture is denatured for 10 minutes in 70° C. water bath and incubated for 1 hour at 37° C., before placing on a prewarmed (37° C.) slide, which is previously denatured in 70% formamide/2×SSC at 70° C., and dehydrated in ethanol series, chilled to 4° C.

Slides are incubated for 16 hours at 37° C. in a humidified chamber. Slides are washed in 50% formamide/2×SSC for 10 minutes at 41° C. and 2×SSC for 7 minutes at 37° C. Hybridization probe is detected by incubation of the slides with FITC-Avidin (ONCOR, Gaithersberg, Md), according to the manufacturer protocol. Chromosomes are counterstained with propridium iodine suspended in mounting medium. Slides are visualized using a Leitz ORTHOPLAN 2-epifluorescence microscope and five computer images are taken using Imagenetics Computer and MacIntosh printer.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Polypeptide assays

The present invention also relates to a diagnostic assays such as quantitative and diagnostic assays for detecting levels of HC gp39-L protein in cells and tissues, including determination of normal and abnormal levels. Thus, for instance, a diagnostic assay in accordance with the invention for detecting over-expression of HC gp39-L protein compared to normal control tissue samples may be used to detect the presence of rheumatoid and osteoarthritis, osteoporosis, artherosclerosis, metastatic cancers, periodontia, chronic renal diseases etc., for example. Assay techniques that can be used to determine levels of a protein, such as an HC gp39-L protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to HC gp39-L, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any HC gp39-L proteins attached to the polystyrene dish. Unbound monoclonal antibody is washed out with buffer. The reporter antibody linked to horseradish peroxidase is placed in the dish resulting in binding of the reporter antibody to any monoclonal antibody bound to HC gp39-L. Unattached reporter antibody is then washed out. Reagents for peroxidase activity, including a calorimetric substrate are then added to the dish. Immobilized peroxidase, linked to HC gp39-L through the primary and secondary antibodies, produces a colored reaction product. The amount of color developed in a given time period indicates the amount of HC gp39-L protein present in the sample. Quantitative results typically are obtained by reference to a standard curve.

A competition assay may be employed wherein antibodies specific to HC gp39-L attached to a solid support and labeled HC gp39-L and a sample derived from the host are passed over the solid support and the amount of label detected attached to the solid support can be correlated to a quantity of HC gp39-L in the sample.

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., *Nature* 256:495–497 (1975), the trioma technique, the human B-cell hybridoma technique (Kozbor et al., *Immunology Today* 4:72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Thus, among others, antibodies against HC gp39-L may be employed to treat/inhibit rheumatoid and osteoarthritis, osteoporosis, artherosclerosis, metastatic cancers, periodontia, chronic renal diseases, etc.

HC gp39-L binding molecules and assays

HC gp39-L could be used to isolate proteins which interact with it and this interaction could be a target for interference. Inhibitors of protein-protein interactions between HC gp39-L and other factors could lead to the development of pharmaceutical agents for the modulation of HC gp39-L activity.

Thus, this invention also provides a method for identification of binding molecules to HC gp39-L. Genes encoding proteins for binding molecules to HC gp39-L can be identified by numerous methods known to those of skill in the art, for example, ligand panning and FACS sorting. Such methods are described in many laboratory manuals such as, for instance, Coligan et al., Current Protocols in Immunology 1(Rivett, A. J. Biochem. J. 291, 1–10 (1993)): Chapter 5 (1991).

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, HC gp39-L cDNA is fused to a Gal4 transcription factor DNA binding domain and expressed in yeast cells. cDNA library members obtained from cells of interest are fused to a transactivation domain of Gal4. cDNA clones which express proteins which can interact with HC gp39-L will lead to reconstitution of Gal4 activity and transactivation of expression of a reporter gene such as Gal1-lacZ.

An alternative method is screening of λgt 11, μZAP (Stratagene) or equivalent cDNA expression libraries with recombinant HC gp39-L. Recombinant HC gp39-L protein or fragments thereof are fused to small peptide tags such as FLAG, HSV or GST. The peptide tags can possess convenient phosphorylation sites for a kinase such as heart muscle creatine kinase or they can be biotinylated. Recombinant HC gp39-L can be phosphorylated with $^{32}$[P] or used unlabeled and detected with streptavidin or antibodies against the tags. λgt11cDNA expression libraries are made from cells of interest and are incubated with the recombinant HC gp39-L, washed and cDNA clones isolated which interact with HC gp39-L. See, e.g., T. Maniatis et al, infra.

Another method is the screening of a mammalian expression library in which the cDNAs are cloned into a vector between a mammalian promoter and polyadenylation site and transiently transfected in COS or 293 cells followed by detection of the binding protein 48 hours later by incubation of fixed and washed cells with a labelled HC gp39-L, prefereably iodinated, and detection of bound HC gp39-L by autoradiography. See Sims et al., *Scienice* 241, 585–589 (1988) and McMahan et al., *EMBO J.* 10, 2821–2832 (1991). In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing HC gp39-L bound to the plate. Cells which attach after washing are lysed and the plasmid DNA isolated, amplified in bacteria, and the cycle of transfection and panning repeated until a single cDNA clone is obtained. See Seed et al, *Proc. Natl. Acad. Sci. USA* 84, 3365 (1987) and Aruffo et al., *EMBO J.* 6, 3313 (1987). If the binding protein is secreted, its cDNA can be obtained by a similar pooling strategy once a binding or neutralizing assay has been established for assaying supernatants from transiently transfected cells. General methods for screening supernatants are disclosed in Wong et a., *Science* 228, 810–815 (1985).

Another alternative method is isolation of proteins interacting with HC gp39-L directly from cells. Fusion proteins of HC gp39-L with GST or small peptide tags are made and immobilized on beads. Biosynthetically labeled or unlabeled protein extracts from the cells of interest are prepared, incubated with the beads and washed with buffer. Proteins interacting with HC gp39-L are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another alternative method is immunoaffinity purification. Recombinant HC gp39-L is incubated with labeled or unlabeled cell extracts and immunoprecipitated with anti-HC gp39-L antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. Recombinant tagged or labeled HC gp39-L is used to select peptides from a peptide or phosphopeptide library which interact with HC gp39-L. Sequencing of the peptides leads to identification of consensus peptide sequences which might be found in interacting proteins.

HC gp39-L binding partners identified by any of these methods or other methods which would be known to those of ordinary skill in the art as well as those putative binding partners discussed above can be used in the assay method of the invention. Assaying for the presence of HC gp39-L/ binding partner complex are accomplished by, for example, the yeast two-hybrid system, ELISA or immunoassays using antibodies specific for the complex. In the presence of test substances which interrupt or inhibit formation of HC gp39-L/binding partner interaction, a decreased amount of complex will be determined relative to a control lacking the test substance.

Assays for free HC gp39-L or binding partner are accomplished by, for example, ELISA or immunoassay using specific antibodies or by incubation of radiolabeled HC gp39-L with cells or cell membranes followed by centrifugation or filter separation steps. In the presence of test substances which interrupt or inhibit formation of HC gp39-Libinding partner interaction, an increased amount of free HC gp39-L or free binding partner will be determined relative to a control lacking the test substance.

Polypeptides of the invention also can be used to assess HC gp39-L binding capacity of HC gp39-L binding molecules in cells or in cell-free preparations.

Agonists and antagonists—assays and molecules

The HC gp39-L of the present invention may be employed in a process for screening for compounds which activate (agonists) or inhibit activation (inhibitors/antagonists) of the polypeptide of the present invention.

Examples of potential HC gp39-L antagonists are an antibody, or in some cases an oligonucleotide, which binds to HC gp39-L that the activity of the polypeptide is prevented.

Potential antagonists also include proteins which are closely related to the binding molecules (such as substrate) of the HC gp39-L, i.e. a fragment of the binding molecules, which have lost biological function and when bind to the HC gp39-L polypeptide, inhibit its activity.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., *Nucl. Acids Res.*, 6:3073 (1979); Cooney et al, *Science*, 241:456 (1988); and Dervan et al., *Science* 251: 1360 (1991)), thereby preventing transcription and the production of HC gp39-L polypeptide. The antisense RNA oligonucleotide hybridizes to the mRNA in vivo and blocks translation of the mRNA molecule into the HC gp39-L polypeptide (antisense—Okano, *J. Neurochem.* 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the HC gp39-L polypeptide.

Another potential antagonist is a small molecule which binds to the HC gp39-L receptor, making it inaccessible to binding molecules (e.g. substrates) such that normal biological activity is prevented. Examples of small molecules include, but are not limited to, small peptides or peptide-like molecules.

HC gp39-L are ubiquitous in the mammalian host and are responsible for many biological functions, including many pathologies. Accordingly, it is desirous to find compounds and drugs which stimulate the HC gp39-L on the one hand and which can inhibit the function of a HC gp39-L on the other hand.

In general, agonists for HC gp39-L polypeptide are employed for therapeutic and prophylactic uses for rheumatoid and osteoarthritis, osteoporosis, artherosclerosis, metastatic cancers, periodontia, chronic renal diseases, etc.

Antagonists/inhibitors for HC gp39-L may be employed for a variety of therapeutic and prophylactic uses for rheumatoid and osteoarthritis, osteoporosis, artherosclerosis, metastatic cancers, periodontia, chronic renal diseases, etc.

This invention additionally provides a method of treating an abnormal condition related to an excess of HC gp39-L activity which comprises administering to a subject the inhibitor compounds (antagonists) as hereinabove described along with a pharmaceutically acceptable carrier in an amount effective to inhibit its activity by blocking binding of binding molecules HC gp39-L polypeptide.

The invention also provides a method of treating abnormal conditions related to an under-expression of HC gp39-L activity which comprises administering to a subject a therapeutically effective amount of a compound which activates the polypeptide of the present invention (agonists) as described above in combination with a pharmaceutically acceptable carrier, to thereby alleviate the abnormal conditions.

Compositions and Kits

The soluble form of the HC gp39-L, and compounds which activate or inhibit such polypeptide, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also relates to compositions comprising the polynucleotide or the polypeptides discussed above. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

The invention further relates to pharmaceutical packs and kits comprising one or more containers filled with one or more of the ingredients of the aforementioned compositions of the invention.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes, among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

Gene therapy

The HC gp39-L polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., *Biotechniques* 7:980–990 (1989), or any other promoter (e.g., cellular promoters such as eukaryotic cellular promoters including, but not limited to, the histone, RNA polymerase III, and $\beta$-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the $\beta$-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., Human Gene Therapy 1: 5–14 (1990). The vector may be transduced into the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Transgenic Animals

The present invention also provides a method for the production of transgenic animals with altered HC gp39-L for the productions of animals bearing HC gp39-L induced diseases. Transgenic, non-human, animals may be obtained by transfecting appropriate fertilized eggs or embryos of a host with nucleic acids encoding HC gp39-L disclosed herein, see for example U.S. Pat. Nos. 4,736,866; 5,175,385; 5,175,384 and 5,175,386. The resultant transgenic animal may be used as a model for the study of altered HC gp39-L. Particularly, useful transgenic animals are those which display a detectable phenotype associated with the altered expression of the HC gp39-L polypeptide. Drugs may then be screened for their ability to reverse or exacerbate the relevant phenotype.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples are carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below is carried out using standard techniques of agarose and polyacrylamide gel electrophoresis ("PAGE") in Sambrook and numerous other references such as, for instance, by Goeddel et al., Nucleic Acids Res. 8:4057 (1980).

Unless described otherwise, ligations are accomplished using standard buffers, incubation temperatures and times, approximately equimolar amounts of the DNA fragments to be ligated and approximately 10 units of T4 DNA ligase ("ligase") per 0.5 $\mu$g of DNA.

Example 1

Procedure for Amplifying gp39like from Thymus cDNA by PCR

The following is the PCR protocol amplifying HC gp39L from Thymus cDNA.

Primer Sequences:
1 5' GCCAAGGATATCGGAGCAACCACCATGGACC 3' SEQ ID NO: [6] (creates an EcoRV restriction site for subcloning)
2 5' CAGGCAGCAAGGTCATCTAGACTGCTTCTCTG 3' SEQ ID NO: [7] (creates an Xba I restriction site for subcloning)

Reaction set up as follows: (Expand High Fidelity Kit-Boehringer Mannheim)
Thymus cDNA (made from poly A$^+$ RNA (Clonetech)) 50 ng
10×PCR Buffer+MgCl$_2$ (supplied with kit)
primer #1 1 ug
primer #2 1 ug
dNTPs (10 mM each mix—dATP, dCTP, dTTP, dGTP) 2 ul
Expand High Fidelity Enzyme 2 Units
H$_2$O 100 ul Total Volume
PCR program:
94° C. for 5 minutes
(94° C. for 1 minute, 52° C. for 1 minute, 72° C. for 1 minute) 34 cycles
72° C. for 10 minutes Example 2

Expression of HC gp-39L in vitro

Recombinant HC gp-39 was produced in vitro by transfecting an expression vector containing the cDNA into CHO cells and selecting stable cell lines.

The full length HC gp-39 gene was cloned into CDN in two pieces; a 660 bp Sac II-Bst EII fragment plus a 678 bp Bst EII-Bcl fragment, ligated together with the CDN vector cut with Sac II-Bcl I. This construct was transfected into CHO ACC 317 Cells by standard methods. Specifically, 20 $\mu$g of the HC gp-39 plasmid construct was linearized by restriction digestion and electroporated into 1.25×10$^7$ cell in 1 ml. Cells were seeded at a density of 2.5×10$^3$ cells per well and selected in minimal media in the absence of nucleosides. Secreted protein was recovered from the conditioned media and purified using Q sepharose flow through, S sepharose capture and sized on Suprose 12. The resulting material was greater than 95% pure as determined by Coomassie blue staining. HC gp-39L can also be expressed as using a similar technique described in this Example 2.

Example 3

Production of polyclonal antibodies generated against HC gp-39L

A partial HC gp-39L protein has been expressed in E. coli and used to generate polyclonal antiserum. A 1461 bp NdeI-XhoI cDNA fragment of HC gp-39L was cloned in frame as a fusion with an N-terminal His tag in the Pet 16B vector system (Novagen). These constructs were transformed into E. coli through standard methods. The cells were propagated, lysed, and the protein purified by nickel affinity chromatography. The purified fusion protein was used to immunize rabbits for the production of polyclonal antiserum.

Example 4

HC gp-39L is associated with the membrane fraction of lymphocytes

Polyclonal antiserum was used to detect HC gp-39L protein on Western blots. Protein is detected in whole cell lysates of lymphocytes. It is also detected in the membrane fraction, but is not associated with the cytoplasmic fraction or secreted into the media. HC gp-39L may function as a cell surface lymphocyte marker for a subset of activated lymphocytes (inflammatory or tissue remodeling diseases) and be detected by FACS analysis, a secondary detection method known to those of skill in the art.

Example 5

Gene therapeutic expression of HC gp39-L

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

HC gp39-L cDNA capable of expressing active HC gp39-L, is isolated. The ends of the fragment are modified, if necessary, for cloning into the vector. For instance, 5' overhanging may be treated with DNA polymerase to create blunt ends. 3' overhanging ends may be removed using Si nuclease. Linkers may be ligated to blunt ends with T4 DNA ligase.

Equal quantities of the Moloney murine leukemia virus linear backbone and the HC gp39-L fragment are mixed together and joined using T4 DNA ligase. The ligation mixture is used to transform *E. coli* and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the HC gp39-L gene is introduced into the packaging cells by standard techniques. Infectious viral particles containing the HC gp39-L gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce HC gp39-L product, and the biological actions of the protein are conveyed to the host.

It will be clear that the invention may be practiced otherwise than as particularly described in the foregoing description and examples.

Numerous modifications and variations of the present invention are possible in light of the above teachings and, therefore, are within the scope of the appended claims.

What is claimed is:

1. An isolated polynucleotide encoding a polypeptide comprising amino acids of SEQ ID NO:2.

2. An isolated polynucleotide comprising the nucleotide sequence of SEQ ID NO:5.

3. An isolated polynucleotide comprising a naturally occurring allelic variant of a polynucleotide encoding the polypeptide comprising SEQ ID NO: 2.

4. An isolated polynucleotide comprising a naturally occurring allelic variant of a polynucleotide comprising SEQ ID NO: 5.

5. The polynucleotide of any one of claims 1, 2, 3 or 4 wherein the polynucleotide is DNA.

6. The polynucleotide of claim 1 wherein the polynucleotide is RNA.

7. The polynucleotide of claim 5 comprising nucleotide 1 to 1433 set forth in SEQ ID NO:1.

8. The polynucleotide of claim 5 comprising nucleotide 52 to 1206 set forth in SEQ ID NO:1.

9. The polynucleotide of claim 5 which encodes a polypeptide comprising amino acids of SEQ ID NO:2.

10. A vector comprising the DNA of claim 5.

11. A host cell comprising the vector of claim 10.

12. A process for producing a polypeptide comprising: expressing from the host cell of claim 11 a polypeptide encoded by said DNA.

13. The polynucleotide of claim 2 wherein the polynucleotide is DNA.

14. An isolated polynucleotide which is complementary to the polynucleotide of any one of claims 1, 2, 3 or 4.

15. The isolated polynucleotide of claim 1 wherein said nucleotide sequence is the entire length of the RNA transcript of SEQ ID NO:2.

16. The isolated polynucleotide of claim 1 wherein said nucleotide sequence is the coding region of the RNA transcript of SEQ ID NO:2.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 1433 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
AGAGAATGTG TATCCCAGAA GAAGCTGGCC AAGGATATGG GAGCAACCAC CATGGACCAG    60
AAGTCTCTCT GGGCAGGTGT AGTGGTCTTG CTGCTTCTCC AGGGAGGATC TGCCTACAAA   120
CTGGTTTGCT ACTTTACCAA CTGGTCCCAG GACCGGCAGG AACCAGGAAA ATTCACCCCT   180
GAGAATATTG ACCCCTTCCT ATGCTCTCAT CTCATCTATT CATTCGCCAG CATCGAAAAC   240
AACAAGGTTA TCATCAAGGA CAAGAGTGAA GTGATGCTCT ACCAGACCAT CAACAGTCTC   300
AAAACCAAGA ATCCCAAACT GAAAATTCTC TTGTCCATTG GAGGGTACCT GTTTGGTTCC   360
```

| | | | | | |
|---|---|---|---|---|---|
| AAAGGGTTCC | ACCCTATGGT | GGATTCTTCT | ACATCACGCT | TGGAATTCAT | TAACTCCATA | 420
| ATCCTGTTTC | TGAGGAACCA | TAACTTTGAT | GGACTGGATG | TAAGCTGGAT | CTACCCAGAT | 480
| CAGAAAGAAA | ACACTCATTT | CACTGTGCTG | ATTCATGAGT | TAGCAGAAGC | CTTTCAGAAG | 540
| GACTTCACAA | AATCCACCAA | GGAAAGGCTT | CTCTTGACTG | CGGGCGTATC | TGCAGGGAGG | 600
| CAAATGATTG | ATAACAGCTA | TCAAGTGAG | AAACTGGCAA | AAGATCTGGA | TTTCATCAAC | 660
| CTCCTGTCCT | TTGACTTCCA | TGGGTCTTGG | GAAAAGCCCC | TTATCACTGG | CCACAACAGC | 720
| CCTCTGAGCA | AGGGGTGGCA | GGACAGAGGG | CCAAGCTCCT | ACTACAATGT | GGAATATGCT | 780
| GTGGGGTACT | GGATACATAA | GGGAATGCCA | TCAGAGAAGG | TGGTCATGGG | CATCCCCACA | 840
| TATGGGCACT | CCTTCACACT | GGCCTCTGCA | GAAACCACCG | TGGGGCCCC | TGCCTCTGGC | 900
| CCTGGAGCTG | CTGGACCCAT | CACAGAGTCT | TCAGGCTTCC | TGGCCTATTA | TGAGATCTGC | 960
| CAGTTCCTGA | AAGGAGCCAA | GATCACGCGG | CTCCAGGATC | AGCAGGTTCC | CTACGCAGTC | 1020
| AAGGGGAACC | AGTGGGTGGG | CTATGATGAT | GTGAAGAGTA | TGGAGACCAA | GGTTCAGTTC | 1080
| TTAAAGAATT | TAAACCTGGG | AGGAGCCATG | ATCTGGTCTA | TTGACATGGA | TGACTTCACT | 1140
| GGCAAATCCT | GCAACCAGGG | CCCTTACCCT | CTTGTCCAAG | CAGTCAAGAG | AAGCCTTGGC | 1200
| TCCCTGTGAA | GGATTAACTT | ACAGAGAAGC | AGGCAAGATG | ACCTTGCTGC | CTGGGGCCTG | 1260
| CTCTCTCCCA | GGAATTCTCA | TGTGGGATTC | CCCTTGCCAG | GATGGCCTTT | GGATCTCTCT | 1320
| TCCAAGCCTT | TCCTGACTTC | CTCTTAGATC | ATAGATTGGA | CCTGGTTTTG | TTTTCCTGCA | 1380
| GCTGTTGACT | TGTTGCCCTG | AAGTACAATA | AAAAAATTC | ATTTTGCTCC | AGT | 1433

(2) INFORMATION FOR SEQ ID NO:2:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:2:

```
Met Asp Gln Lys Ser Leu Trp Ala Gly Val Val Leu Leu Leu Leu
  1               5                  10                  15

Gln Gly Gly Ser Ala Tyr Lys Leu Val Cys Tyr Phe Thr Asn Trp Ser
                 20                  25                  30

Gln Asp Arg Gln Glu Pro Gly Lys Phe Thr Pro Glu Asn Ile Asp Pro
             35                  40                  45

Phe Leu Cys Ser His Leu Ile Tyr Ser Phe Ala Ser Ile Glu Asn Asn
     50                  55                  60

Lys Val Ile Ile Lys Asp Lys Ser Glu Val Met Leu Tyr Gln Thr Ile
 65                  70                  75                  80

Asn Ser Leu Lys Thr Lys Asn Pro Lys Leu Lys Ile Leu Leu Ser Ile
                 85                  90                  95

Gly Gly Tyr Leu Phe Gly Ser Lys Gly Phe His Pro Met Val Asp Ser
                100                 105                 110

Ser Thr Ser Arg Leu Glu Phe Ile Asn Ser Ile Ile Leu Phe Leu Arg
```

|     |     |     | 115 |     |     |     | 120 |     |     |     | 125 |     |     |     |
|-----|-----|-----|-----|-----|-----|-----|-----|-----|-----|-----|-----|-----|-----|-----|

Asn His Asn Phe Asp Gly Leu Asp Val Ser Trp Ile Tyr Pro Asp Gln
    130                     135                 140

Lys Glu Asn Thr His Phe Thr Val Leu Ile His Glu Leu Ala Glu Ala
145             150                 155                     160

Phe Gln Lys Asp Phe Thr Lys Ser Thr Lys Glu Arg Leu Leu Leu Thr
                165                 170                 175

Ala Gly Val Ser Ala Gly Arg Gln Met Ile Asp Asn Ser Tyr Gln Val
            180              185                 190

Glu Lys Leu Ala Lys Asp Leu Asp Phe Ile Asn Leu Leu Ser Phe Asp
        195             200                 205

Phe His Gly Ser Trp Glu Lys Pro Leu Ile Thr Gly His Asn Ser Pro
    210             215                 220

Leu Ser Lys Gly Trp Gln Asp Arg Gly Pro Ser Ser Tyr Tyr Asn Val
225                 230                 235                 240

Glu Tyr Ala Val Gly Tyr Trp Ile His Lys Gly Met Pro Ser Glu Lys
            245                 250                 255

Val Val Met Gly Ile Pro Thr Tyr Gly His Ser Phe Thr Leu Ala Ser
            260                 265                 270

Ala Glu Thr Thr Val Gly Ala Pro Ala Ser Gly Pro Gly Ala Ala Gly
        275                 280                 285

Pro Ile Thr Glu Ser Ser Gly Phe Leu Ala Tyr Tyr Glu Ile Cys Gln
    290                 295                 300

Phe Leu Lys Gly Ala Lys Ile Thr Arg Leu Gln Asp Gln Val Pro
305                 310                 315                 320

Tyr Ala Val Lys Gly Asn Gln Trp Val Gly Tyr Asp Asp Val Lys Ser
                325                 330                 335

Met Glu Thr Lys Val Gln Phe Leu Lys Asn Leu Asn Leu Gly Gly Ala
        340                 345                 350

Met Ile Trp Ser Ile Asp Met Asp Asp Phe Thr Gly Lys Ser Cys Asn
        355                 360                 365

Gln Gly Pro Tyr Pro Leu Val Gln Ala Val Lys Arg Ser Leu Gly Ser
    370                 375                 380

Leu
385

( 2 ) INFORMATION FOR SEQ ID NO:3:

( i ) SEQUENCE CHARACTERISTICS:
        ( A ) LENGTH: 1526 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

AGAGAATGTG TATCCCAGAA GAAGCTGGCC AAGGATATGG GAGCAACCAC CATGGACCAG    60

AAGTCTCTCT GGGCAGGTGT AGTGGTCTTG CTGCTTCTCC AGGGAGAGAT GGGGTTTTGC   120

TATGTTGCCA GAGCTGGTCT TGAACTCCTG GGCTCAAGAA GTCCTCCTGC CTCAGCCTCC   180

| | | | | | |
|---|---|---|---|---|---|
| CAAAGTGCTG | GGATAACAGG | ATCTGCCTAC | AAACTGGTTT | GCTACTTTAC | CAACTGGTCC | 240
| CAGGACCGGC | AGGAACCAGG | AAAATTCACC | CCTGAGAATA | TTGACCCCTT | CCTATGCTCT | 300
| CATCTCATCT | ATTCATTCGC | CAGCATCGAA | AACAACAAGG | TTATCATCAA | GGACAAGAGT | 360
| GAAGTGATGC | TCTACCAGAC | CATCAACAGT | CTCAAAACCA | AGAATCCAA | ACTGAAAATT | 420
| CTCTTGTCCA | TTGGAGGGTA | CCTGTTTGGT | TCCAAAGGGT | TCCACCCTAT | GGTGGATTCT | 480
| TCTACATCAC | GCTTGGAATT | CATTAACTCC | ATAATCCTGT | TTCTGAGGAA | CCATAACTTT | 540
| GATGGACTGG | ATGTAAGCTG | GATCTACCCA | GATCAGAAAG | AAAACACTCA | TTTCACTGTG | 600
| CTGATTCATG | AGTTAGCAGA | AGCCTTTCAG | AAGGACTTCA | CAAAATCCAC | CAAGGAAAGG | 660
| CTTCTCTTGA | CTGCGGGCGT | ATCTGCAGGG | AGGCAAATGA | TTGATAACAG | CTATCAAGTT | 720
| GAGAAACTGG | CAAAAGATCT | GGATTTCATC | AACCTCCTGT | CCTTTGACTT | CCATGGGTCT | 780
| TGGGAAAAGC | CCCTTATCAC | TGGCCACAAC | AGCCCTCTGA | GCAAGGGGTG | GCAGGACAGA | 840
| GGGCCAAGCT | CCTACTACAA | TGTGGAATAT | GCTGTGGGGT | ACTGGATACA | TAAGGGAATG | 900
| CCATCAGAGA | AGGTGGTCAT | GGGCATCCCC | ACATATGGGC | ACTCCTTCAC | ACTGGCCTCT | 960
| GCAGAAACCA | CCGTGGGGGC | CCCTGCCTCT | GGCCCTGGAG | CTGCTGGACC | CATCACAGAG | 1020
| TCTTCAGGCT | TCCTGGCCTA | TTATGAGATC | TGCCAGTTCC | TGAAAGGAGC | CAAGATCACG | 1080
| CGGCTCCAGG | ATCAGCAGGT | TCCCTACGCA | GTCAAGGGA | ACCAGTGGGT | GGGCTATGAT | 1140
| GATGTGAAGA | GTATGGAGAC | CAAGGTTCAG | TTCTTAAAGA | ATTTAAACCT | GGGAGGAGCC | 1200
| ATGATCTGGT | CTATTGACAT | GGATGACTTC | ACTGGCAAAT | CCTGCAACCA | GGGCCCTTAC | 1260
| CCTCTTGTCC | AAGCAGTCAA | GAGAAGCCTT | GGCTCCCTGT | GAAGGATTAA | CTTACAGAGA | 1320
| AGCAGGCAAG | ATGACCTTGC | TGCCTGGGGC | CTGCTCTCTC | CCAGGAATTC | TCATGTGGGA | 1380
| TTCCCCTTGC | CAGGATGGCC | TTTGGATCTC | TCTTCCAAGC | CTTTCCTGAC | TTCCTCTTAG | 1440
| ATCATAGATT | GGACCTGGTT | TTGTTTTCCT | GCAGCTGTTG | ACTTGTTGCC | CTGAAGTACA | 1500
| ATAAAAAAAA | TTCATTTTGC | TCCAGT | | | | 1526

( 2 ) INFORMATION FOR SEQ ID NO:4:

( i ) SEQUENCE CHARACTERISTICS:
        ( A ) LENGTH: 416 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:4:

```
Met Asp Gln Lys Ser Leu Trp Ala Gly Val Val Leu Leu Leu Leu
 1               5                  10                  15

Gln Gly Glu Met Gly Phe Cys Tyr Val Ala Arg Ala Gly Leu Glu Leu
                20                  25                  30

Leu Gly Ser Arg Ser Pro Pro Ala Ser Ala Ser Gln Ser Ala Gly Ile
            35                  40                  45

Thr Gly Ser Ala Tyr Lys Leu Val Cys Tyr Phe Thr Asn Trp Ser Gln
        50                  55                  60

Asp Arg Gln Glu Pro Gly Lys Phe Thr Pro Glu Asn Ile Asp Pro Phe
```

|     |     |     |     | 65  |     |     |     |     | 70  |     |     |     |     | 75  |     |     |     |     | 80  |
| --- | --- | --- | --- | --- | --- | --- | --- | --- | --- | --- | --- | --- | --- | --- | --- | --- | --- | --- | --- |
| Leu | Cys | Ser | His | Leu | Ile | Tyr | Ser | Phe | Ala | Ser | Ile | Glu | Asn | Asn | Lys |
|     |     |     |     | 85  |     |     |     |     | 90  |     |     |     |     | 95  |     |
| Val | Ile | Ile | Lys | Asp | Lys | Ser | Glu | Val | Met | Leu | Tyr | Gln | Thr | Ile | Asn |
|     |     |     | 100 |     |     |     |     | 105 |     |     |     |     | 110 |     |     |
| Ser | Leu | Lys | Thr | Lys | Asn | Pro | Lys | Leu | Lys | Ile | Leu | Leu | Ser | Ile | Gly |
|     |     |     | 115 |     |     |     | 120 |     |     |     |     | 125 |     |     |     |
| Gly | Tyr | Leu | Phe | Gly | Ser | Lys | Gly | Phe | His | Pro | Met | Val | Asp | Ser | Ser |
|     |     |     | 130 |     |     | 135 |     |     |     |     | 140 |     |     |     |     |
| Thr | Ser | Arg | Leu | Glu | Phe | Ile | Asn | Ser | Ile | Ile | Leu | Phe | Leu | Arg | Asn |
| 145 |     |     |     |     | 150 |     |     |     | 155 |     |     |     |     |     | 160 |
| His | Asn | Phe | Asp | Gly | Leu | Asp | Val | Ser | Trp | Ile | Tyr | Pro | Asp | Gln | Lys |
|     |     |     |     | 165 |     |     |     |     | 170 |     |     |     |     | 175 |     |
| Glu | Asn | Thr | His | Phe | Thr | Val | Leu | Ile | His | Glu | Leu | Ala | Glu | Ala | Phe |
|     |     |     | 180 |     |     |     |     | 185 |     |     |     |     | 190 |     |     |
| Gln | Lys | Asp | Phe | Thr | Lys | Ser | Thr | Lys | Glu | Arg | Leu | Leu | Leu | Thr | Ala |
|     |     | 195 |     |     |     |     | 200 |     |     |     |     | 205 |     |     |     |
| Gly | Val | Ser | Ala | Gly | Arg | Gln | Met | Ile | Asp | Asn | Ser | Tyr | Gln | Val | Glu |
|     |     | 210 |     |     |     |     | 215 |     |     |     |     | 220 |     |     |     |
| Lys | Leu | Ala | Lys | Asp | Leu | Asp | Phe | Ile | Asn | Leu | Leu | Ser | Phe | Asp | Phe |
| 225 |     |     |     |     | 230 |     |     |     |     | 235 |     |     |     |     | 240 |
| His | Gly | Ser | Trp | Glu | Lys | Pro | Leu | Ile | Thr | Gly | His | Asn | Ser | Pro | Leu |
|     |     |     |     | 245 |     |     |     |     | 250 |     |     |     |     | 255 |     |
| Ser | Lys | Gly | Trp | Gln | Asp | Arg | Gly | Pro | Ser | Ser | Tyr | Tyr | Asn | Val | Glu |
|     |     |     | 260 |     |     |     |     | 265 |     |     |     |     | 270 |     |     |
| Tyr | Ala | Val | Gly | Tyr | Trp | Ile | His | Lys | Gly | Met | Pro | Ser | Glu | Lys | Val |
|     |     | 275 |     |     |     |     | 280 |     |     |     |     | 285 |     |     |     |
| Val | Met | Gly | Ile | Pro | Thr | Tyr | Gly | His | Ser | Phe | Thr | Leu | Ala | Ser | Ala |
|     | 290 |     |     |     |     | 295 |     |     |     |     | 300 |     |     |     |     |
| Glu | Thr | Thr | Val | Gly | Ala | Pro | Ala | Ser | Gly | Pro | Gly | Ala | Ala | Gly | Pro |
| 305 |     |     |     |     | 310 |     |     |     |     | 315 |     |     |     |     | 320 |
| Ile | Thr | Glu | Ser | Ser | Gly | Phe | Leu | Ala | Tyr | Tyr | Glu | Ile | Cys | Gln | Phe |
|     |     |     |     | 325 |     |     |     |     | 330 |     |     |     |     | 335 |     |
| Leu | Lys | Gly | Ala | Lys | Ile | Thr | Arg | Leu | Gln | Asp | Gln | Gln | Val | Pro | Tyr |
|     |     |     | 340 |     |     |     |     | 345 |     |     |     |     | 350 |     |     |
| Ala | Val | Lys | Gly | Asn | Gln | Trp | Val | Gly | Tyr | Asp | Asp | Val | Lys | Ser | Met |
|     |     | 355 |     |     |     |     | 360 |     |     |     |     | 365 |     |     |     |
| Glu | Thr | Lys | Val | Gln | Phe | Leu | Lys | Asn | Leu | Asn | Leu | Gly | Gly | Ala | Met |
|     |     | 370 |     |     |     |     | 375 |     |     |     |     | 380 |     |     |     |
| Ile | Trp | Ser | Ile | Asp | Met | Asp | Asp | Phe | Thr | Gly | Lys | Ser | Cys | Asn | Gln |
| 385 |     |     |     |     | 390 |     |     |     |     | 395 |     |     |     |     | 400 |
| Gly | Pro | Tyr | Pro | Leu | Val | Gln | Ala | Val | Lys | Arg | Ser | Leu | Gly | Ser | Leu |
|     |     |     |     | 405 |     |     |     |     | 410 |     |     |     |     | 415 |     |

( 2 ) INFORMATION FOR SEQ ID NO:5:

( i ) SEQUENCE CHARACTERISTICS:
        ( A ) LENGTH: 3742 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

| | | | | | | |
|---|---|---|---|---|---|---|
| GCCAAGGCAG | GAGGGGCGCT | TGAGCCCAGG | AATTCAAGAC | CAGCCTGGGT | AATGTAGTGA | 60 |
| GACCCTGTNT | NNACAAATTT | TTTTTTTTT | TTTTAATTAG | CAAGGTGTAA | GGTGCATGCC | 120 |
| TGTGGNTCCA | GCTACTCTGG | AGGCCAAGCT | GGGAAGATCC | TTTGAGCCCG | GGAGGTTGAG | 180 |
| GNTGCAGTGA | GCCATGATGG | TGCCATTGCA | CTCCAATTGG | GGTGATACAG | CAAGAGCAAG | 240 |
| ATCCTGTTTC | TAAAAAAATT | AAGCAAGCCA | GAGGTGGCTG | TGAACACAGA | GAGAGGTCGG | 300 |
| GGGCATAGAA | GAAGGAGACA | GATTGGGATG | ATGAGGAAGG | AGATTCAGGG | CCGAGGGTGA | 360 |
| TACCAGGAGG | CAGAGCCTGA | GTATCACCTC | CTTCCCTTCT | CCAGGACCGG | GTCCCTTTTA | 420 |
| GGTGAGACTA | GATGAAAAGG | GCTCTTCAGC | AGCTGACTTC | ACAGCAACTA | ATTTCTGACA | 480 |
| GGTCAGAGTT | GGCATTGCTC | AAATCTGGGC | TTCATTTCCA | AGAAGTTTCA | CAAGTACTGC | 540 |
| CAGGGGAAGT | ACCCTGGACT | TCTTGCTTCT | TTCGTGTAGG | ACAGGCTGTC | GAAACCTCAG | 600 |
| TGGATAAAAG | ACCTAGAGAA | TGTGTATCCC | AGAAGAAGCT | GGCCAAGGAT | ATGGGAGCAA | 660 |
| CCACCATGGA | CCAGAAGTCT | CTCTGGGCAG | GTGAGCATGG | GGTTGATAAT | TCAGCAGGAA | 720 |
| AGTTGGTGAG | GAAGGAAGAG | GTAACAGGTC | TGTAGAAGAA | GTAATCTTCC | TCCTTTCCTG | 780 |
| GGACTTCAGT | CTTTCCGTTG | ACCTTAGTGT | CAAAAAATTT | CAAGCCAATG | CAACTGTTGT | 840 |
| AGGGGAACCA | CCTGATCTTT | CCTGAATGGA | CAAAAATGCA | GCAGTAGCCA | GAACCCTTTG | 900 |
| CACTGGCAGG | ATGTTCTCAG | TTTGTGCAGA | GGTCCTTCTT | GTCCACATTA | GAACTGGAGC | 960 |
| TAAGACAGGA | AAGAGGCCAA | GCTTTCTTAG | TCTCTTGGTG | TATGAGCGTT | GTATTGCGAG | 1020 |
| TCACATCTTT | CTTGGGCTCT | GCTGTGGTTA | TATTTTACAA | CTTTTGGAGA | GCCCCACATT | 1080 |
| TCTCATCTGC | AGAATGGTTT | ATTGAATTTA | ATGTTTTTA | AACTCTCCCT | TTCAACTCTA | 1140 |
| AAGTTCTGAT | CCAAAACTCT | GGCTTTTGTG | GTGGCTGGGA | ATTGGGATGA | GAGTGGGGAT | 1200 |
| GAGGCTAAAT | AAACAAGGCT | ATGAGTGAAC | GGGGACGTT | TACCAGGAGG | GGAGGGGAGG | 1260 |
| GAATATGTCT | GCTGGAGGAA | AGAAATCATT | TATTTGTGTC | CATACCTCTT | TCACCCTTGT | 1320 |
| CTTACCCTCT | CAAGCCATGA | AGCCCCCACT | TGGCAAGAGC | CTTTTGGGTT | CCTGTTGAAC | 1380 |
| TTAGCTGAGC | CCTGGACTGA | CCCTTGACAG | GGTAGAGCCC | GTAGGGAGGC | CACACTTTGG | 1440 |
| AGAAGGGCCT | GGAGGCTGAC | CTGACAGTGG | ATGTGCCACA | GAGAATTTCT | CTGACCATTT | 1500 |
| ACTTAGTGAG | TGTGTGGAGA | ACCAGGGCCT | AACCTCCCTG | CCTAAAAAAA | CATGTGAGTC | 1560 |
| ATCAAGAGAG | AACAGTAGAG | CCCTGTTTTC | CAGCCCTAAG | CTCTGCAGGG | GAGGAATCAG | 1620 |
| CTCCAGCAGC | TGTGTCATTG | AAAGTTTTCT | CTCCTTTTTG | GCTGCCCCTT | TCTTCACTTT | 1680 |
| TGGACCCGTA | AAGGTTTCAG | AGTGAACAAT | ATCCCCAGGC | TGGGGGGATT | GCAGTTCCAG | 1740 |
| GAGTCTTGTC | CATTGGGCAA | AGTTTCTAGG | ATCCAGGGGT | CTGCTCTTTT | TTTCCTTTAG | 1800 |
| GAGGATGTGT | TAAGTATAGA | ATAATCTCAC | CAGTCTTCCT | AGGGTAGATG | TCCTATGGAG | 1860 |
| AAGAGACTGG | GCATAATTTC | AAACATATAA | GTTTAAAGCA | CTACCAGGGC | CAGCTCACAC | 1920 |
| TGCTTATCTT | GTTCTAAGAG | TTAATTGTTT | ATACATAGTG | GGACCATCTC | AATTTGCCTG | 1980 |
| AGATAGTTCT | GGTTCAAGCT | ATCGTCCTAG | GGAAATTATT | AATAATGTTC | CTTTTTACTC | 2040 |
| TTTGAAGGGT | CTCATTGGAC | AATAAACTAT | ATGGTCACCC | TACCTATATT | CAACTCCAGA | 2100 |
| CTGGACTATG | AGCTCCTTGA | GTGCAGGGAA | GGCATTAACT | GCATTATAAT | TTCCCCAGTG | 2160 |
| TCCTGAGCAA | TGCTTAGCAC | AGAGCATATG | ATTCAATAAA | ACTTTGTTGG | ATAAATGAAT | 2220 |

-continued

| | | | | | |
|---|---|---|---|---|---|
|GAAAAAATAA|ATTCCCAGCT|TGGAACATGT|TTCTGCCTAG|GAATGTAGAG|ACACAAGGCA|2280
|CCCCAGGGCT|GGGGACCTCA|AGGTCCTATA|AAGAAACCAC|AGGCCGGGCG|CGGTGGCTCA|2340
|CGCCTGTAAT|CCCAGCACTT|TGGGAGGCCG|AGGCGGGCGG|ATCACGAGGT|CAGGAGATCG|2400
|AGACCATCCC|GGCTAAAACG|GTGAAACCCC|GTCTCTACTA|AAAATACAAA|AAATTAGCCG|2460
|GGCGTAGTGG|CGGGCGCCTG|TAGTCCCAGC|TACTTGGGAG|GCTGAGGCAG|GAGAATGGCG|2520
|TGAACCCGGG|AGGCGGAGCT|TGCAGTGAGC|CGAGATCACA|CCACTGCACT|CCAGCCTGGG|2580
|CGACAGAGCG|AGACTCCGTC|TCAAAAAAAA|AAAAAAAAAA|AGAAACCACA|GCAGCTGTGG|2640
|CTGGGGAGCC|CAGATGAAGT|GTGGCTCTAT|CTTGTATGTG|AGCACACCCA|CATTTTCACT|2700
|GCCATTATCT|GGGACAGCAG|AACCAGGTTT|GGCTCAACAG|ATTTCTCTTT|CCACCCATCT|2760
|ATTGCAGGAG|TAGTGGTCTT|GCTGCTTCTC|CAGGGAGGTA|AGTAGTCAAT|AAGTCACTAC|2820
|CGCCTGGATC|TCCTGGCTTG|GGTGCTTTCA|TTTTGATGT|ACAGTTTCTT|TTTCTGCTAC|2880
|ATGCTTTTTC|TCTTGATTAC|TCTCTCCGGT|TCTGCCACTG|ACATATTTAT|GACACTGAGT|2940
|TTTTATTCTA|TCTTTTTGTG|TATCCCTTGT|TCTAGTTCTT|TTTGAGCCAC|TCTCTCTCTC|3000
|ACCCCTCCCC|CATAGCTGGC|CTCAATATGT|GTGTGTGAAT|ACAAACATAC|ACAATGTTTG|3060
|TATTATCTGT|TTCTCTACTG|ATCTGTGTCA|TCCATCCATA|CATACATACT|GAATCTTAGT|3120
|GCTCCATGGG|TGTTTCATAT|GTTGGTGGTA|TCTCTGTCTC|TCAATGTATT|TTTTTTTTAA|3180
|TTTTTTTGAG|ACAGGGTCTC|ACTGTAAGGT|CCAGGCTGTA|GTGCAGTGGT|GTGACCNTGG|3240
|CTCANTGCAG|CCTTGACCTC|CCAGGCTCAA|ACAATCCCCC|AACTTCAGCC|TCCTTAGTAG|3300
|CTGAGANTAC|AGGCATGAAC|CACTACACCT|GGCTAATTNT|TAAATTTTTT|GTAGAGATGG|3360
|GGTTTTGCTA|TGTTGCCACA|GCTGGTCTTG|AACTCCTGGG|CTCAAGAAGT|CNTCNNGCNT|3420
|CAGCCTCCCA|AAGTGCNGGG|ATAACAGGTN|TGAGGCCACT|GTGCCCAGCC|TCAGCGTATT|3480
|TCTTAACTGG|GGTCTGGGTA|CTCAAGAGCC|AGCACTAAAG|GCCCAGGCAG|AATGACCCTC|3540
|AGAGGCTCTG|GCAGAATGAG|CAAATGATGC|AATGGCTGTA|CTTGGGGAGA|AAATTGTGAC|3600
|TTTCTGGACT|CTAAGGCAAC|AGCCGTGAGA|TCTCACTGGC|TCTCTTCATT|CTACTCCAGG|3660
|GATCTGCCTA|CAAACTGGTT|TGCTACTTTA|CCAACTGGTC|CCAGGACCGG|CAGGAACCAG|3720
|GAAAATTCAC|CCCTGAGAAT|AT| | | |3742

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

| | | | |
|---|---|---|---|
|GCCAAGGATA|TCGGAGCAAC|CACCATGGAC|C|31

( 2 ) INFORMATION FOR SEQ ID NO:7:

( i ) SEQUENCE CHARACTERISTICS:
        ( A ) LENGTH: 32 base pairs ( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:7:

CAGGCAGCAA GGTCATCTAG ACTGCTTCTC TG 32